(12) United States Patent
Subramanian et al.

(10) Patent No.: US 8,940,510 B2
(45) Date of Patent: Jan. 27, 2015

(54) SPRAY DRIED MICROBES AND METHODS OF PREPARATION AND USE

(75) Inventors: Venkiteswaran Subramanian, Coralville, IA (US); James H. Glenn, IV, Lone Tree, CO (US); Shuvendu Das, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 433 days.

(21) Appl. No.: 12/742,890

(22) PCT Filed: Nov. 16, 2007

(86) PCT No.: PCT/US2007/024074
§ 371 (c)(1),
(2), (4) Date: Sep. 10, 2010

(87) PCT Pub. No.: WO2009/064277
PCT Pub. Date: May 22, 2009

(65) Prior Publication Data
US 2010/0330630 A1    Dec. 30, 2010

(51) Int. Cl.
C12P 7/50 (2006.01)
C12P 7/42 (2006.01)
C12N 1/00 (2006.01)
C12P 21/06 (2006.01)
C07H 21/04 (2006.01)
C12N 11/16 (2006.01)
C12N 9/04 (2006.01)
C12N 9/08 (2006.01)
C12N 9/96 (2006.01)
C12P 7/40 (2006.01)

(52) U.S. Cl.
CPC ............. *C12N 11/16* (2013.01); *C12N 9/0006* (2013.01); *C12N 9/0065* (2013.01); *C12N 9/96* (2013.01); *C12P 7/40* (2013.01); *C12P 7/42* (2013.01); *C12Y 111/01006* (2013.01)
USPC ...... 435/143; 435/146; 435/243; 435/254.11; 435/254.2; 435/254.21; 435/254.23; 435/69.1; 536/23.2

(58) Field of Classification Search
USPC ................. 435/143, 146, 243, 254.11, 254.2, 435/254.21, 254.23, 69.1; 536/23.2
See application file for complete search history.

(56) References Cited

U.S. PATENT DOCUMENTS

| 5,866,382 | A | 2/1999 | Hallborn |
| 6,146,879 | A | 11/2000 | Liddell et al. |
| 6,846,657 | B2 | 1/2005 | Heikkila et al. |
| 6,924,133 | B1 | 8/2005 | Jørgensen et al. |
| 7,109,005 | B2 | 9/2006 | Eroma et al. |
| 2006/0110809 | A1 | 5/2006 | Taylor et al. |
| 2006/0246563 | A1 | 11/2006 | Eroma et al. |
| 2007/0031919 | A1 | 2/2007 | Dunson et al. |
| 2008/0009044 | A1* | 1/2008 | Cohen et al. .................. 435/119 |
| 2008/0032376 | A1 | 2/2008 | Bach |
| 2009/0291483 | A1 | 11/2009 | Bach et al. |

FOREIGN PATENT DOCUMENTS

| CN | 1382213 A | 11/2002 |
| EP | 0450430 A2 | 10/1991 |
| EP | 0450430 A3 | 10/1991 |
| EP | 0450430 B1 | 6/1997 |
| WO | WO-2007010403 A2 | 1/2007 |
| WO | WO-2009/064277 A1 | 5/2009 |
| WO | WO-2009/070822 A2 | 6/2009 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Santivarangkna et al., Alternative drying processes for the industrial preservation of of lactic acid starter cultures. Biotechnol. Prog. 2007, vol. 23: 302-315.*
"International Application Serial No. PCT/US2007/024074 International Search Report and Written Opinion mailed Aug. 14, 2008", 15 pgs.
Gough, S., et al., "Production of pyruvate from lactate using recombinant *Pichia pastoris* cells as catalyst", *Process Biochemistry, Elsevier, NL*; vol. 40(8), (Jul. 1, 2005), 2597-2601.
"Chinese Application Serial No. 200780102228.X, Response filed Sep. 16, 2012 to Office Action mailed May 2, 2012", 9 pgs.
"Chinese Application Serial No. 200780102228.X,Office Action mailed Mar. 29, 2013", (w/ English Translation), 10 pgs.
"Chinese Application Serial No. 200780102228.X, Office Action mailed Oct. 25, 2012", 8 pgs.
"Chinese Application Serial No. 200780102228.X, Response filed Jan. 7, 2013 to Office Action mailed Oct. 25, 2012", (w/ English Translation of Claims), 9 pgs.

(Continued)

*Primary Examiner* — Ganapathirama Raghu
(74) *Attorney, Agent, or Firm* — Schwegman Lundberg & Woessner, P.A.

(57) ABSTRACT

The invention provides spray-dried preparations of microbes and methods of using those microbes.

20 Claims, 22 Drawing Sheets

(56) References Cited

OTHER PUBLICATIONS

"Chinese Application Serial No. 200780102228.X, Decision on Rejection mailed Aug. 16, 2013", (w/ English Translation), 12 pgs.

"Chinese Application Serial No. 200780102228.X, Response filed Nov. 26, 2013 to Office Action mailed Aug. 16, 2013", 6 pgs.

Santivarangka, Chalat, et al., "Alternative Drying Processes for the Industrial Preservation of Lactic Acid Starter Cultures", Biotechnology Progress, 23(2), (2007), 302-315.

"Chinese Application Serial No. 2007810102228.X, Office Action mailed Nov. 3, 2011", (w/ English Translation), 18 pgs.

"European Application Serial No. 07862075.4, Office Action mailed Nov. 15, 2010", 5 pgs.

"European Application Serial No. 07862075.4, Response filed Mar. 16, 2011 to Office Action mailed Nov. 15, 2010", 6 pgs.

Nidetzky, B., et al., "Continuous enzymatic production of xylitol with simultaneous coenzyme regeneration in a charged membrane reactor", *Biotechnol Bioeng*, 52(3), (Nov. 5, 1996), 387-96.

Straathof, A. J, et al., "The production of fine chemicals by biotransformations", *Current Opinion in Biotechnology*, 13(6), (Dec. 2002), 548-556.

"Chinese Application Serial No. 200780102228.X, Office Action mailed Mar. 14, 2014", 3 pgs.

"Chinese Application Serial No. 200780102228.X, Reexamination Decision mailed Mar. 4, 2014", w/English translation, 2 pgs.

"Chinese Application Serial No. 200780102228.X, Response filed May 20, 2014 to Office Action mailed Mar. 14, 2014", w/English claims, 8 pgs.

"Chinese Application Serial No. 200780102228.X, Response filed Jul. 9, 2013 to Office Action mailed Mar. 29, 2013", w/English claims, 8 pgs.

"European Application Serial No. 07862075.4, Amendment filed Aug. 9, 2010", 5 pgs.

"Indian Application Serial No. 3006/CHENP/2010, First Examiner Report mailed Jul. 22, 2014", 2 pgs.

"International Application Serial No. PCT/US2007/024074, Preliminary Report on Patentability mailed May 18, 2010", 8 pgs.

Golowczyc, M. A, et al., "Preservation of probiotic strains isolated from kefir by spray drying", Letters in Applied Microbiology, 50(1), (2010), 7-12.

Golowczyc, Marina A, et al., "Cellular injuries of spray-dried Lactobacillus spp. isolated from kefir and their impact on probiotic properties", International Journal of Food Microbiology, 144(3), Abstract, (Jan. 5, 2011), 2 pgs.

Yanez-Mendizabal, V., et al., "Endospore production allows using spray-drying as a possible formulation system of the biocontrol agent Bacillus subtilis CPA-8", Biotechnology Letters, 34(4), Abstract, (Apr. 2012), 2 pgs.

\* cited by examiner

SPRAY DRIED MICROBES AND METHODS OF PREPARATION AND USE

RELATED APPLICATION

This patent application is a U.S. National Stage Filing under 35 U.S.C. 371 from International Patent Application Serial No. PCT/US2007/024074, filed Nov. 16, 2007, and published on May 22, 2009, as WO 2009/064277 A1, the contents of which are incorporated herein by reference in their entirety.

BACKGROUND

Glyoxylic acid and other keto acids such as pyruvic acid are important intermediates in the manufacture of various agrochemicals, pharmaceuticals and fragrances. Typical commercial production of glyoxylic acid employs either oxidation chemistry or electrochemistry. Electrochemical manufacture involves either the reduction of oxalic acid or the anodic oxidation of glyoxal to form glyoxylic acid whereas chemical oxidation generally involves the oxidation of glyoxal in the presence of a strong acid such as $HNO_3$. A consequence of these commercial processes is the production of waste streams containing various toxic acids and heavy metals.

Glycolate oxidase is an enzyme available from various sources, including green leafy plants and mammalian cells, which catalyzes the oxidation of glycolic acid to glyoxylic acid, with the concomitant production of hydrogen peroxide. For instance, Tolbert et al., *J. Biol. Chem.*, 181:905 (1949), reported an enzyme, extracted from tobacco leaves, which catalyzed the oxidation of glycolic acid to formic acid and $CO_2$ via the intermediate formation of glyoxylic acid. The addition of certain compounds, such as ethylenediamine, limited the further oxidation of the intermediate glyoxylic acid. The oxidations were carried out at a pH of about 8, typically using glycolic acid concentrations of about 3-40 mM (millimolar). The optimum pH for the glycolate oxidation was reported to be pH 8.9. Oxalic acid (100 mM) was reported to inhibit the catalytic action of the glycolate oxidase. Similarly, Richardson and Tolbert, *J. Biol. Chem.*, 236:1280 (1961), reported the formation of oxalic acid during the glycolate oxidase-catalyzed oxidation of glycolic acid to glyoxylic acid, using enzymes isolated from tobacco, sugar beet, Swiss chard, spinach, or rat liver. Richardson and Tolbert, *J. Biol. Chem.*, 236:1280 (1961), also showed that buffers containing tris(hydroxymethyl)aminomethane (TRIS) inhibited the formation of oxalic acid in the glycolate oxidase catalyzed oxidation of glycolic acid. Clagett et al., *J. Biol. Chem.*, 78:977 (1949) reported that the optimum pH for the glycolate oxidase catalyzed oxidation of glycolic acid with oxygen was about 7.8-8.6, and the optimum temperature was 35°-40° C.

Recent advances in recombinant DNA technology, combined with the isolation of cDNA coding for the spinach glycolate oxidase (see Volokita et al, *J. Biol. Chem.*, 262: 15825 (1987)), have allowed for the construction of microbial strains that are intended to serve as alternative, economic enzyme sources. For instance, yeast offers several advantages to commercial applications over *Escherichia coli* and other bacteria. Yeast can generally be grown to higher densities than bacteria and are readily adaptable to continuous fermentation processing. It has been reported, for example, that *Pichia pastoris* can be grown to cell densities in excess of 100 g/L (U.S. Pat. No. 4,414,329). Additional advantages of yeast hosts include the fact that many critical functions of the organism, such as oxidative phosphorylations, are located within organelles and thus are not exposed to the possible deleterious effects of the overexpression of foreign enzymatic products. Furthermore, yeasts appear to be capable of glycosylation of expressed polypeptide products, where such glycosylation is important to the bioactivity of the polypeptide product.

Zelitch and Ochoa, *J. Biol. Chem.*, 201:707 (1953), and Robinson et al., *J. Biol. Chem.*, 237:2001 (1962), reported that the formation of formic acid and $CO_2$ in the spinach glycolate oxidase-catalyzed oxidation of glycolic acid resulted from the nonenzymatic reaction of $H_2O_2$ with glyoxylic acid. They observed that addition of catalase, an enzyme that catalyzes the decomposition of $H_2O_2$, greatly improved the yields of glyoxylic acid by suppressing the formation of formic acid and $CO_2$. With respect to glyoxylic acid production in yeast, glyoxylic acid was produced when glycolic acid and oxygen were reacted in an aqueous solution in the presence of aminomethylphosphonic acid and a catalyst which is a genetically-engineered microbial yeast transformant which expresses the enzyme glycolate oxidase from spinach ((S)-2-hydroxy-acid oxidase, EC 1.1.3.15), and catalase (EC 1.11.1.6) (see U.S. Pat. No. 5,693,490).

SUMMARY OF THE INVENTION

The invention provides spray-dried preparations of microbial cells such as bacterial and yeast cells, or lysates or crude extracts thereof, suitable for biocatalysis. Spray-drying of microbial cells, such as *Pichia*, *Saccharomyces* or *E. coli*, renders the cells suitable for biocatalysis via opening of the cell wall or cell membrane in the absence of permeabilization agents allowing for substrates and products to freely move in and out of the cells. Thus, one or more enzymes useful in biocatalysis may be expressed in microbes, e.g., recombinantly expressed, and those cells spray-dried. Spray drying results in microbial cells that are porous but have structural integrity, e.g., enzymes do not readily leach out of spray-dried cells, in enzymes that are stable at room temperature, and permits processing in water rather than a buffer at a particular pH. The stability and lack of leaching of enzymes from spray-dried microbial cells allows for repeated use of the cells over time, e.g., continuous and extended use of a single preparation of spray-dried cells. In one embodiment, spray-dried microbial cells having at least two enzymes for a coupled reaction are provided. In one embodiment, spray-dried microbial cells, e.g., yeast cells suitable for pyruvate or glycolate production, such as those expressing glycolate oxidase and catalase, are provided. In one embodiment, spray-dried microbial cells such as yeast cells suitable for pyruvate or glycolate production have recombinant glycolate oxidase, e.g., a heterologous glycolate oxidase. In one embodiment, spray-dried microbial cells suitable for pyruvate or glycolate production have recombinant catalase, e.g., a heterologous catalase. For example, in one embodiment, spray-dried *Pichia* cells have spinach glycolate oxidase and *Sacharromyces* catalase T. However, the invention is not limited to particular microbes and/or particular enzyme catalyzed reactions, as it is contemplated that microbes generally, whether recombinant or nonrecombinant, may be spray-dried and result in a source of stable enzyme(s) for biocatalysis.

The use of spray-dried microbial cells may reduce the number of process steps for biocatalysis-based product production. For instance, the number of steps for glycolate oxidase-mediated production of several products has been reduced by at least 2- to 3-fold using spray-dried microbial cells, thereby providing a simpler process and significant cost advantages. In one embodiment, a microbial cell suspension may be spray-dried directly from the fermentor, thus eliminating a solid/liquid separation step. For example, the cell containing solution directly from the fermentor (without separation) may be spray-dried or first subjected to cell separation and resuspension, e.g., in water or a buffer, prior to spray drying.

The invention provides a method to prepare a whole microbial cell biocatalyst preparation. The method includes providing a microbial cell suspension and spray drying the microbial cell suspension under conditions effective to yield a spray-dried microbial cell preparation suitable for biocatalysis. In one embodiment, a spray-dried preparation of yeast is provided. In one embodiment, a spray-dried preparation of *Pichia* or *Saccharomyces* is provided In one embodiment, the spray-dried preparation of yeast has at least one recombinant enzyme encoded by an expression cassette having a promoter operably linked to an open reading frame for the enzyme. The methods for preparing the spray-dried microbial cell biocatalyst surprisingly do not require detergent or other membrane permeabilization agent treatment, e.g., do not require a cationic surfactant, such as benzylalkonium chloride (BAC), treatment, or enzyme stabilizing agents such as sucrose, trehalose, thiols or other polyols.

Further provided is a method to prepare products of an enzymatic reaction. The method includes combining a spray-dried preparation of the invention and an aqueous solution comprising a substrate for an enzyme present in the spray-dried preparation under conditions that yield one or more products of the enzyme catalyzed reaction. In one embodiment, the product is pyruvic acid or its salts, which are useful in food, pharmaceutical and agrochemical products, e.g., in dietary supplements, cosmetics or oxygenated solvents, and production of amino acids, hydrazone, indoxocarb and indole-3-pyruvic acid.

For example, a spray-dried preparation of yeast having recombinant glycolate oxidase is combined with an aqueous solution comprising a substrate for the enzyme under conditions that yield a product of the enzyme catalyzed reaction. Products of the reaction, for instance, pyruvate, glyoxylate, keto acids or chiral hydroxyl acids, are then isolated from the aqueous medium.

In one embodiment, the invention provides spray-dried preparations of microbes having enzymes that provide chiral resolution or enantiomeric selectivity.

DETAILED DESCRIPTION OF THE INVENTION

Definitions

Figure 1:
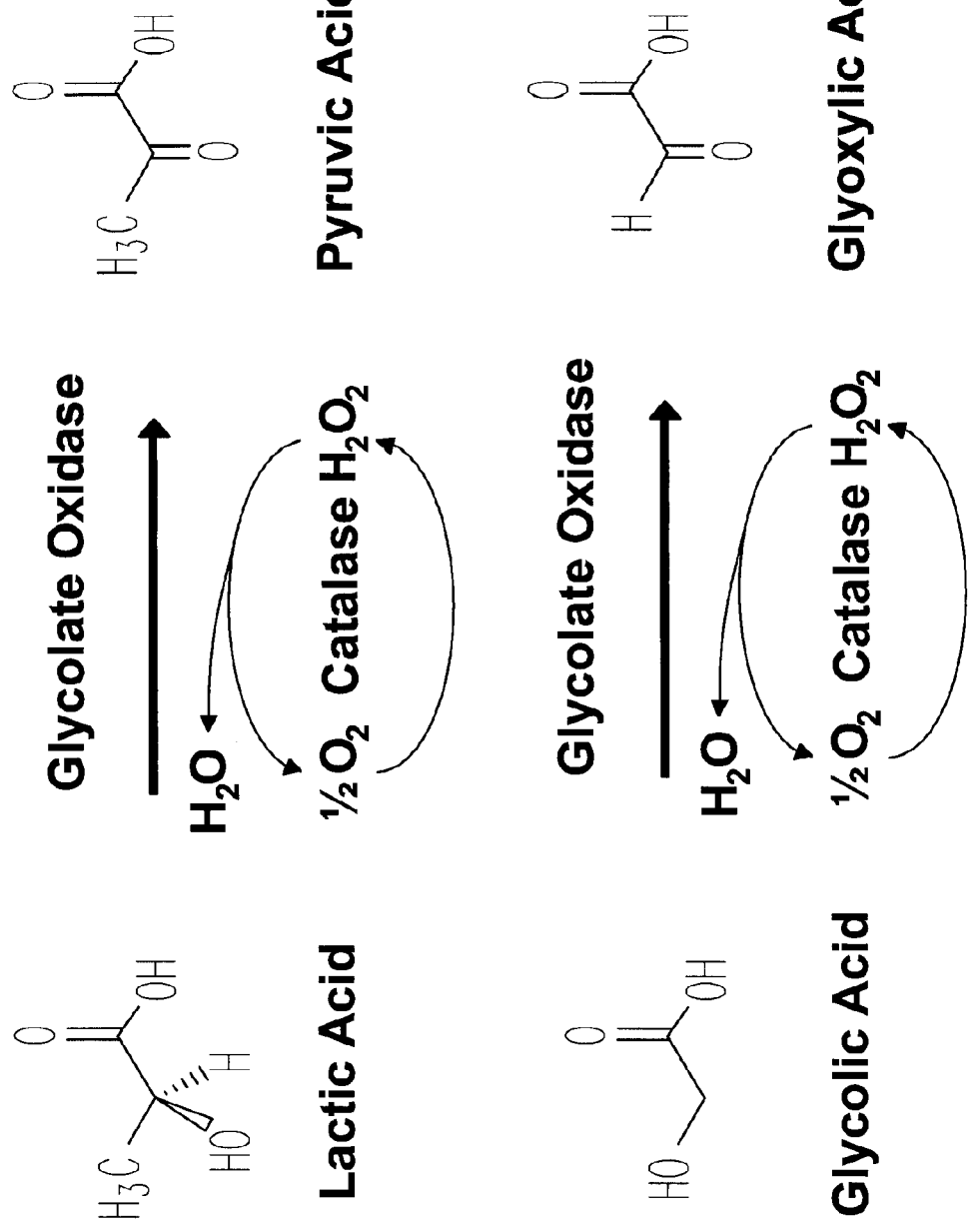
FIG. 1. Glycolate oxidase reactions.
Figure 2A:
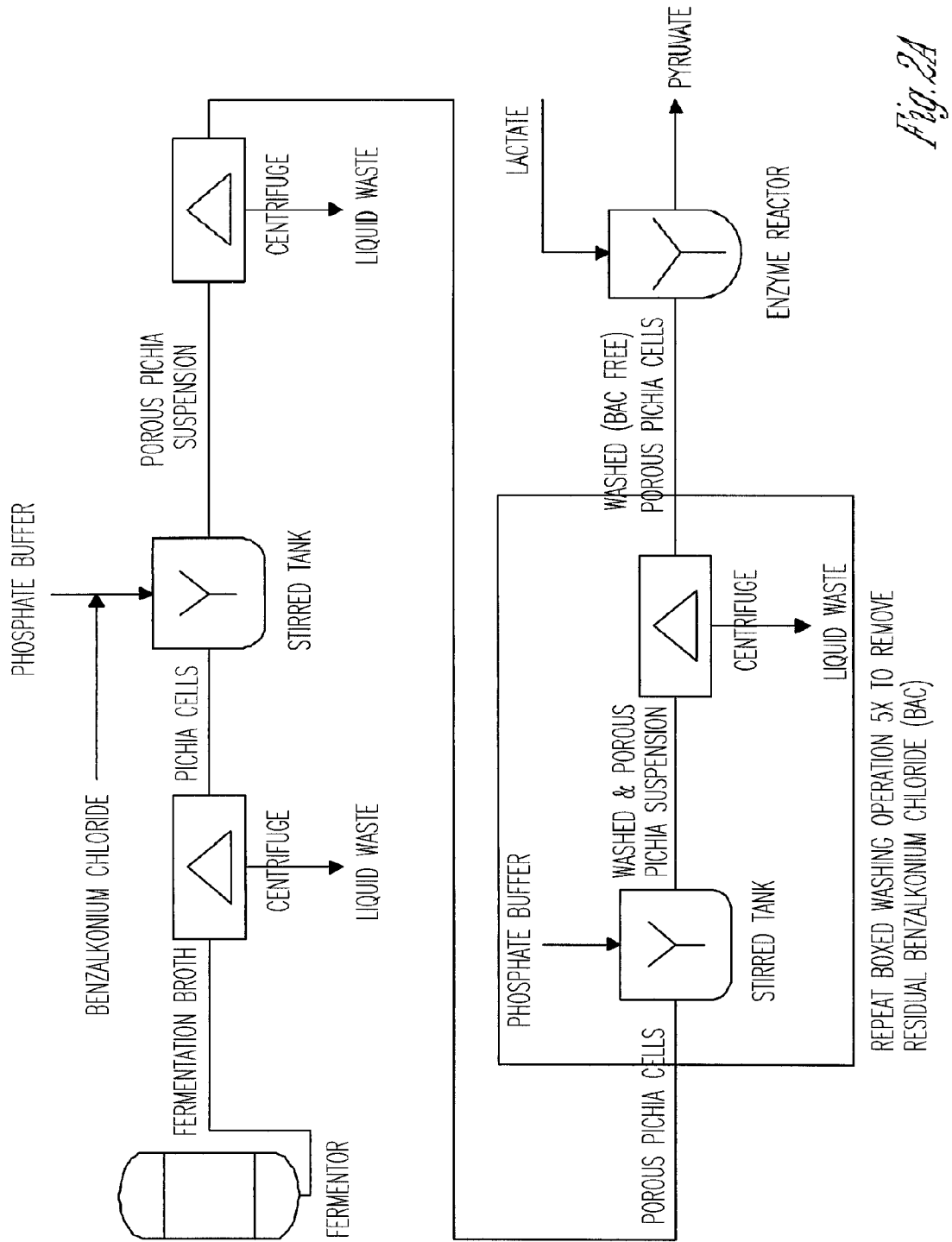
FIG. 2A. Process for producing products of the glycolate oxidase reaction using yeast and benzylalkonium chloride (BAC) treatment.
Figure 2B:
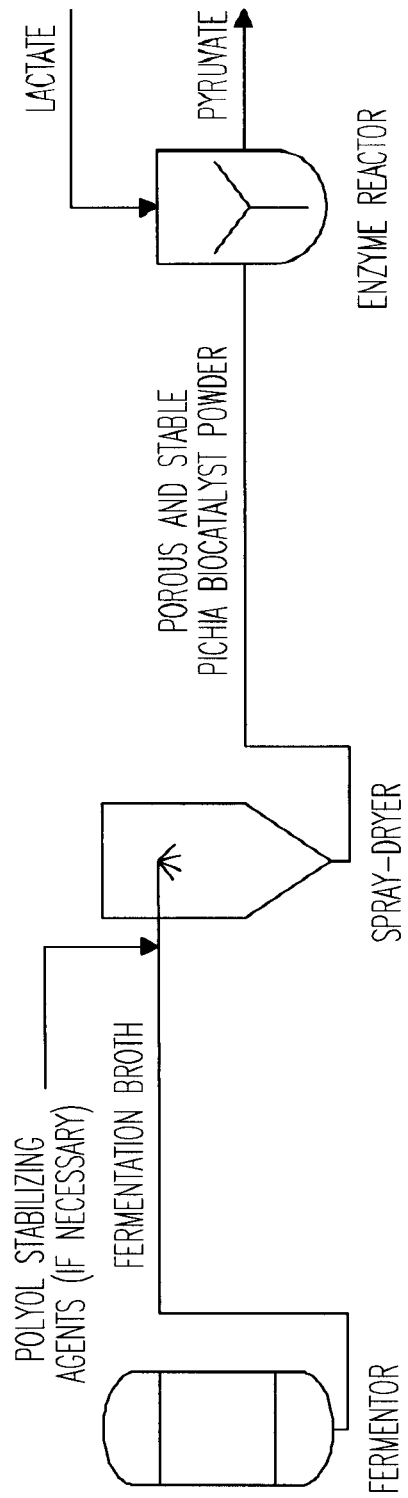
FIG. 2B. Process for producing products of the glycolate oxidase reaction using spray-dried yeast cells.

The term "nucleic acid molecule", "polynucleotide", or "nucleic acid sequence" as used herein, refers to nucleic acid, DNA or RNA, that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides. A "polynucleotide", as used herein, is a nucleic acid containing a sequence that is greater than about 100 nucleotides in length. An "oligonucleotide" or "primer", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene (e.g., open reading frame or coding region) are generally located 5' or upstream of the coding region. However, enhancer elements can exert their effect even when located 3' of the promoter element and the coding region. Transcription termination and polyadenylation signals are located 3' or downstream of the coding region.

The term "codon" as used herein, is a basic genetic coding unit, consisting of a sequence of three nucleotides that specify a particular amino acid to be incorporated into a polypeptide chain, or a start or stop signal. The term "coding region" when used in reference to structural gene refers to the nucleotide sequences that encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

The term "gene" refers to a DNA sequence that comprises coding sequences and optionally control sequences necessary for the production of a polypeptide from the DNA sequence.

As used herein, the term "heterologous" nucleic acid sequence or protein refers to a sequence that relative to a reference sequence has a different source, e.g., originates from a foreign species, or, if from the same species, it may be substantially modified from the original form.

Nucleic acids are known to contain different types of mutations. A "point" mutation refers to an alteration in the sequence of a nucleotide at a single base position from the wild-type sequence. Mutations may also refer to insertion or deletion of one or more bases, so that the nucleic acid sequence differs from a reference, e.g., a wild-type, sequence.

As used herein, the terms "hybridize" and "hybridization" refer to the annealing of a complementary sequence to the target nucleic acid, i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenylation signal and optionally an enhancer sequence.

A polynucleotide having a nucleotide sequence encoding a protein or polypeptide means a nucleic acid sequence comprising the coding region of a gene, or in other words the nucleic acid sequence encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The term "transcription regulatory element" or "transcription regulatory sequence" refers to a genetic element or sequence that controls some aspect of the expression of nucleic acid sequence(s). For example, a promoter is a regulatory element that facilitates the initiation of transcription of an operably linked coding region. Other regulatory elements include, but are not limited to, transcription factor binding sites, splicing signals, polyadenylation signals, termination signals and enhancer elements.

Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types. For example, the SV40 early gene enhancer is very active in a wide variety of cell types from many mammalian species and has been widely used for the expression of proteins in mammalian cells. Two other examples of promoter/enhancer elements active in a broad range of mammalian cell types are those from the human elongation factor 1 gene and the long terminal repeats of the Rous sarcoma virus; and the human cytomegalovirus.

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site. A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/Bcl I restriction fragment and directs both termination and polyadenylation.

Eukaryotic expression vectors may also contain "viral replicons" or "viral origins of replication." Viral replicons are viral DNA sequences that allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (about 100 copies/cell).

The term "in vitro" refers to an artificial environment and to processes or reactions that occur within an artificial environment. In vitro environments include, but are not limited to, test tubes and cell lysates. The term "in vivo" refers to the natural environment (e.g., an animal or a cell) and to processes or reaction that occur within a natural environment.

The term "expression system" refers to any assay or system for determining (e.g., detecting) the expression of a gene of interest. Those skilled in the field of molecular biology will understand that any of a wide variety of expression systems may be used. A wide range of suitable mammalian cells are available from a wide range of source (e.g., the American Type Culture Collection, Rockland, Md.). The method of transformation or transfection and the choice of expression vehicle will depend on the host system selected. Transformation and transfection methods are well known to the art. Expression systems include in vitro gene expression assays where a gene of interest (e.g., a reporter gene) is linked to a regulatory sequence and the expression of the gene is monitored following treatment with an agent that inhibits or induces expression of the gene. Detection of gene expression can be through any suitable means including, but not limited to, detection of expressed mRNA or protein (e.g., a detectable product of a reporter gene) or through a detectable change in the phenotype of a cell expressing the gene of interest. Expression systems may also comprise assays where a cleavage event or other nucleic acid or cellular change is detected.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may single-stranded), but may contain both the sense and antisense strands (i.e., the oligonucleotide may be double-stranded).

By "peptide," "protein" and "polypeptide" is meant any chain of amino acids, regardless of length or post-translational modification (e.g., glycosylation or phosphorylation). The nucleic acid molecules of the invention may also encode a variant of a naturally-occurring protein or polypeptide fragment thereof, which has an amino acid sequence that is at least 85%, 90%, 95% or 99% identical to the amino acid sequence of the naturally-occurring (native or wild-type) protein from which it is derived. The term "fusion polypeptide" or "fusion protein" refers to a chimeric protein containing a reference protein (e.g., luciferase) joined at the N- and/or C-terminus to one or more heterologous sequences (e.g., a non-luciferase polypeptide). In some embodiments, a modified polypeptide, fusion polypeptide or a portion of a full-length polypeptide of the invention, may retain at least some of the activity of a corresponding full-length functional (nonchimeric) polypeptide. In other embodiments, in the absence of an exogenous agent or molecule of interest, a modified polypeptide, fusion polypeptide or portion of a full-length functional polypeptide of the invention, may lack activity relative to a corresponding full-length functional polypeptide. In other embodiments, a modified polypeptide, fusion polypeptide or portion of a full-length functional polypeptide of the invention in the presence of an exogenous agent may retain at least some or have substantially the same activity, or alternatively lack activity, relative to a corresponding full-length functional polypeptide.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. The terms "N-terminal" and "C-terminal" in reference to polypeptide sequences refer to regions of polypeptides including portions of the N-terminal and C-terminal regions of the polypeptide, respectively. A sequence that includes a portion of the N-terminal region of polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminus and C-terminus of the polypeptide, respectively.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention. Optionally, a nucleic acid molecule of the invention may be introduced into a suitable cell line so as to create a stably-transfected cell line capable of producing the protein or polypeptide encoded by the gene. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

The term "homology" refers to a degree of complementarity between two or more sequences. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

The term "purified" or "to purify" means the result of any process that removes some of a contaminant from the component of interest, such as a protein or nucleic acid. The percent of a purified component is thereby increased in the sample.

As used herein, "pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a "substantially pure" composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, a "marker gene" or "reporter gene" is a gene that imparts a distinct phenotype to cells expressing the gene and thus permits cells having the gene to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Elements of the present disclosure are exemplified in detail through the use of particular marker genes. Of course, many examples of suitable marker genes or reporter genes are known to the art and can be employed in the practice of the invention. Therefore, it will be understood that the following discussion is exemplary rather than exhaustive. In light of the techniques disclosed herein and the general recombinant techniques which are known in the art, the present invention renders possible the alteration of any gene. Exemplary modified reporter proteins are encoded by nucleic acid molecules comprising modified reporter genes including, but are not limited to, modifications of a neo gene, a β-gal gene, a gus gene, a cat gene, a gpt gene, a hyg gene, a hisD gene, a ble gene, a mprt gene, a bar gene, a nitrilase gene, a galactopyranoside gene, a xylosidase gene, a thymidine kinase gene, an arabinosidase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a β-lactamase gene, a xylE gene, an α-amylase gene, a tyrosinase gene, a luciferase (luc) gene, (e.g., a *Renilla reniformis* luciferase gene, a firefly luciferase gene, or a click beetle luciferase (*Pyrophorus plagiophthalamus*) gene), an aequorin gene, a red fluorescent protein gene, or a green fluorescent protein gene.

All amino acid residues identified herein are in the natural L-configuration. In keeping with standard polypeptide nomenclature, abbreviations for amino acid residues are as shown in the following Table of Correspondence.

TABLE OF CORRESPONDENCE

| 1-Letter | 3-Letter | AMINO ACID |
|---|---|---|
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

Sources of Cells for Spray-Drying and Methods of Preparation and Use

The invention provides spray-dried preparations of microbial cells, or lysates or crude extracts thereof, suitable for biocatalysis, and a simpler process for using those cells, lysates or crude extracts thereof, in biocatalysis. In one embodiment of the invention, the invention provides for spray-dried preparations of prokaryotic cells, or lysates or crude extracts thereof, suitable for biocatalysis, and a simpler process for using those cells, lysates or crude extracts thereof, in biocatalysis. In one embodiment, the prokaryotic cells are *E. coli* cells. In another embodiment, the prokaryotic cells are *Pseudomonas* cells.

The invention also provides spray-dried preparations of yeast suitable for biocatalysis and a simpler process for using those cells in biocatalysis. For example, previously for production of pyruvate and glyoxylate by a recombinant *P. pastoris* having glycolate oxidase and catalase, the cells were harvested, washed, treated with benzylalkonium chloride (BAC) to make the cells porous to substrates such as lactate and glycolate, and washed several times to remove any residual BAC, and used for the production of pyruvate and glyoxylate (about 6 to 8 steps).

The present invention provides for a process to spray-dry microbial cells to render them porous and suitable for biocatalysis, without leaching of enzymes for the biocatalysis. Thus, the cells can be used directly for production. Accordingly, the process to take a biocatalyst from the fermentor to the reactor has been simplified by several steps. Spray-drying the cells may also render the enzymes in those cells stable. As described herein for recombinant cells with glycolate oxidase and catalase, spray drying did not result in enzyme leaching or a need to treat with BAC. Also, spray drying resulted in stable enzymes and did not compromise the selectivity of glycolate oxidase towards various α-hydroxyacids, as the spray-dried enzyme is active on S-acids (i.e., oxidizes S-acids) but is not active towards R-acids, i.e., the spray-dried enzyme is selective for S-acids not R-acids. Thus, kinetic resolution of chiral compound, for example, racemic α-hydroxyacids is also possible with the spray-dried preparations described herein. Accordingly, the invention provides microbial cells such as yeast cells, e.g., *Pichia* or *Saccharomyces* cells, as well as recombinant microbial cells, such as recombinant *Pichia*, *Pseudomonas* or *E. coli* cells, for the production of various chemicals and resolution of enantiomers. The spray-dried cells are easy to prepare, store and use.

Yeast cells useful in the present invention are those from phylum Ascomycota, subphylum Saccharomycotina, class Saccharomycetes, order Saccharomycetales or Schizosaccharomycetales, family Saccharomycetaceae, genus *Saccharomyces* or *Pichia* (*Hansenula*), e.g., species: *P. anomola*, *P. guilliermondii*, *P. norvegenesis*, *P. ohmeri*, and *P. pastoris*. Yeast cells employed in the invention may be native (non-recombinant) cells or recombinant cells, e.g., those which are transformed with exogenous (recombinant) DNA having one or more expression cassettes each with a polynucleotide having a promoter and an open reading frame encoding one or more enzymes useful for biocatalysis. The enzyme(s) encoded by the exogenous DNA is referred to as "recombinant," and that enzyme may be from the same species or heterologous (from a different species). For example, a recombinant *P. pastoris* cell may recombinantly express a *P. pastoris* enzyme or a plant, microbial, e.g., *Aspergillus* or *Saccharomyces*, or mammalian enzyme.

In one embodiment, the microbial cell employed in the methods of the invention is transformed with recombinant DNA, e.g., in a vector. Vectors, plasmids, cosmids, YACs (yeast artificial chromosomes) BACs (bacterial artificial chromosomes) and DNA segments for use in transforming cells will generally comprise DNA encoding an enzyme, as well as other DNA that one desires to introduce into the cells. These DNA constructs can further include elements such as promoters, enhancers, polylinkers, marker or selectable genes, or even regulatory genes, as desired. For instance, one of the DNA segments or genes chosen for cellular introduction will often encode a protein that will be expressed in the resultant transformed (recombinant) cells, such as to result in a screenable or selectable trait and/or that will impart an improved phenotype to the transformed cell. However, this may not always be the case, and the present invention also encompasses transformed cells incorporating non-expressed transgenes.

DNA useful for introduction into cells includes that which has been derived or isolated from any source, that may be subsequently characterized as to structure, size and/or function, chemically altered, and later introduced into cells. An example of DNA "derived" from a source, would be a DNA sequence that is identified as a useful fragment within a given organism, and that is then chemically synthesized in essentially pure form. An example of such DNA "isolated" from a source would be a useful DNA sequence that is excised or removed from said source by biochemical means, e.g., enzymatically, such as by the use of restriction endonucleases, so that it can be further manipulated, e.g., amplified, for use in the invention, by the methodology of genetic engineering. Such DNA is commonly also referred to as "recombinant DNA."

Therefore, useful DNA includes completely synthetic DNA, semi-synthetic DNA, DNA isolated from biological sources, and DNA derived from introduced RNA. The introduced DNA may be or may not be a DNA originally resident in the host cell genotype that is the recipient of the DNA (native or heterologous). It is within the scope of the invention to isolate a gene from a given genotype, and to subsequently introduce multiple copies of the gene into the same genotype, e.g., to enhance production of a given gene product.

The introduced DNA includes, but is not limited to, DNA from genes such as those from bacteria, yeasts, fungi, plants or vertebrates, e.g., mammals. The introduced DNA can include modified or synthetic genes, e.g., "evolved" genes, portions of genes, or chimeric genes, including genes from the same or different genotype. The term "chimeric gene" or "chimeric DNA" is defined as a gene or DNA sequence or segment comprising at least two DNA sequences or segments from species that do not combine DNA under natural conditions, or which DNA sequences or segments are positioned or linked in a manner that does not normally occur in the native genome of the untransformed cell.

The introduced DNA used for transformation herein may be circular or linear, double-stranded or single-stranded. Generally, the DNA is in the form of chimeric DNA, such as plasmid DNA, which can also contain coding regions flanked by regulatory sequences that promote the expression of the recombinant DNA present in the transformed cell. For example, the DNA may include a promoter that is active in a cell that is derived from a source other than that cell, or may utilize a promoter already present in the cell that is the transformation target.

Generally, the introduced DNA will be relatively small, i.e., less than about 30 kb to minimize any susceptibility to physical, chemical, or enzymatic degradation that is known to increase as the size of the DNA increases. The number of proteins, RNA transcripts or mixtures thereof that is introduced into the cell is preferably preselected and defined, e.g., from one to about 5-10 such products of the introduced DNA may be formed.

The selection of an appropriate expression vector will depend upon the host cells. An expression vector can contain, for example, (1) prokaryotic DNA elements coding for a bacterial origin of replication and an antibiotic resistance gene to provide for the amplification and selection of the expression vector in a bacterial host; (2) DNA elements that control initiation of transcription such as a promoter; (3) DNA elements that control the processing of transcripts such as introns, transcription termination/polyadenylation sequence; and (4) a gene of interest that is operatively linked to the DNA elements to control transcription initiation. The expression vector used may be one capable of autonomously replicating in the host cell or capable of integrating into the chromosome, originally containing a promoter at a site enabling transcription of the linked gene.

Yeast or fungal expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences. Several well-characterized yeast expression systems are known in the art and described in, e.g., U.S. Pat. No. 4,446,235, and European Patent Applications 103,409 and 100,561. A large variety of shuttle vectors with yeast promoters are also known to the art. However, any other plasmid or vector may be used as long as they are replicable and viable in the host.

The construction of vectors that may be employed in conjunction with the present invention will be known to those of skill of the art in light of the present disclosure (see, e.g., Sambrook and Russell, *Molecular Biology: A Laboratory Manual*, 2001). The expression cassette of the invention may contain one or a plurality of restriction sites allowing for placement of the polynucleotide encoding an enzyme. The expression cassette may also contain a termination signal operably linked to the polynucleotide as well as regulatory sequences required for proper translation of the polynucleotide. The expression cassette containing the polynucleotide of the invention may be chimeric, meaning that at least one of its components is heterologous with respect to at least one of the other components. Expression of the polynucleotide in the expression cassette may be under the control of a constitutive promoter, inducible promoter, regulated promoter, viral promoter or synthetic promoter.

The expression cassette may include, in the 5'-3' direction of transcription, a transcriptional and translational initiation region, the polynucleotide of the invention and a transcriptional and translational termination region functional in vivo and/or in vitro. The termination region may be native with the transcriptional initiation region, may be native with the polynucleotide, or may be derived from another source. The regulatory sequences may be located upstream (5' non-coding sequences), within (intron), or downstream (3' non-coding sequences) of a coding sequence, and influence the transcription, RNA processing or stability, and/or translation of the associated coding sequence. Regulatory sequences may include, but are not limited to, enhancers, promoters, repressor binding sites, translation leader sequences, introns, and polyadenylation signal sequences. They may include natural and synthetic sequences as well as sequences that may be a combination of synthetic and natural sequences.

The vector used in the present invention may also include appropriate sequences for amplifying expression.

A promoter is a nucleotide sequence that controls the expression of a coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. A promoter may also include a minimal promoter plus a regulatory element or elements capable of controlling the expression of a coding sequence or functional RNA. This type of promoter sequence contains of proximal and more distal elements, the latter elements are often referred to as enhancers.

Representative examples of promoters include, but are not limited to, promoters known to control expression of genes in prokaryotic or eukaryotic cells or their viruses. For instance, any promoter capable of expressing in yeast hosts can be used as a promoter in the present invention, for example, the GAL4 promoter may be used. Additional promoters useful for expression in a yeast cell are well described in the art. Examples thereof include promoters of the genes coding for glycolytic enzymes, such as TDH3, glyceraldehyde-3-phosphate dehydrogenase (GAPDH), a shortened version of GAPDH (GAPFL), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, invertase and glucokinase genes and the like in the glycolytic pathway, heat shock protein promoter, MFa-1 promoter, CUP 1 promoter, MET, the promoter of the TRP1 gene, the AOX (alcohol oxidase) gene promoter, e.g., the AOX1 or AOX2 promoter, the ADC1 gene (coding for the alcohol dehydrogenase I) or ADR2 gene (coding for the alcohol dehydrogenase II), acid phosphatase (PHO5) gene, isocytochrome c gene, a promoter of the yeast mating pheromone genes coding for the a- or α-factor, or the GAL/CYC1 hybrid promoter (intergenic region of the GAL1-GAL10 gene/Cytochrome1 gene) (Guarente et al. 1982). Promoters with transcriptional control that can be turned on or off by variation of the growth conditions include, e.g., PHO5, ADR2, and GAL/CYC1 promoters. The PHO5 promoter, for example, can be repressed or derepressed at will, solely by increasing or decreasing the concentration of inorganic phosphate in the medium. Some promoters, such as the ADH1 promoter, allow high-level constitutive expression of the gene of interest.

Any promoter capable of expressing in filamentous fungi may be used. Examples are a promoter induced strongly by starch or cellulose, e.g., a promoter for glucoamylase or a-amylase from the genus *Aspergillus* or cellulase (cellobiohydrase) from the genus *Trichoderma*, a promoter for enzymes in the glycolytic pathway, such as phosphoglycerate kinase (pgk) and glyceryaldehyde 3-phosphate dehydrogenase (gpd), etc.

Particular bacterial promoters include but are not limited to *E. coli* lac or trp, the phage lambda $P_L$, lacZ, T3, T7, gpt, and lambda $P_R$ promoters.

Two principal methods for the control of expression are known, viz.: induction, which leads to overexpression, and repression, which leads to underexpression. Overexpression can be achieved by insertion of a strong promoter in a position that is operably linked to the target gene, or by insertion of one or more than one extra copy of the selected gene. For example, extra copies of the gene of interest may be positioned on an autonomously replicating plasmid, such as pYES2.0 (Invitrogen Corp., Carlsbad, Calif.), where overexpression is controlled by the GAL4 promoter after addition of galactose to the medium.

Several inducible promoters are known in the art. Many are described in a review by Gatz, *Curr. Op. Biotech.*, 7:168 (1996) (see also Gatz, *Ann. Rev. Plant. Physiol. Plant Mol. Biol.*, 48:89 (1997)). Examples include tetracycline repressor system, Lac repressor system, copper-inducible systems, salicylate-inducible systems (such as the PR1a system), glucocorticoid-inducible (Aoyama T. et al., 1997), alcohol-inducible systems, e.g., AOX promoters, and ecdysome-inducible systems. Also included are the benzene sulphonamide-inducible (U.S. Pat. No. 5,364,780) and alcohol-inducible (WO 97/06269 and WO 97/06268) inducible systems and glutathione S-transferase promoters.

In addition to the use of a particular promoter, other types of elements can influence expression of transgenes. In particular, introns have demonstrated the potential for enhancing transgene expression.

Other elements include those that can be regulated by endogenous or exogenous agents, e.g., by zinc finger proteins, including naturally occurring zinc finger proteins or chimeric zinc finger proteins. See, e.g., U.S. Pat. No. 5,789,538, WO 99/48909; WO 99/45132; WO 98/53060; WO 98/53057; WO 98/53058; WO 00/23464; WO 95/19431; and WO 98/54311.

An enhancer is a DNA sequence that can stimulate promoter activity and may be an innate element of the promoter or a heterologous element inserted to enhance the level or tissue specificity of a particular promoter. An enhancer is capable of operating in both orientations (5' to 3' and 3' to 5' relative to the gene of interest coding sequences), and is capable of functioning even when moved either upstream or downstream from the promoter. Both enhancers and other upstream promoter elements bind sequence-specific DNA-binding proteins that mediate their effects.

Vectors for use in accordance with the present invention may be constructed to include an enhancer element. Constructs of the invention will also include the gene of interest along with a 3' end DNA sequence that acts as a signal to terminate transcription and allow for the polyadenylation of the resultant mRNA.

As the DNA sequence between the transcription initiation site and the start of the coding sequence, i.e., the untranslated leader sequence, can influence gene expression, one may also wish to employ a particular leader sequence. Preferred leader sequences are contemplated to include those that include sequences predicted to direct optimum expression of the attached gene, i.e., to include a preferred consensus leader sequence that may increase or maintain mRNA stability and prevent inappropriate initiation of translation. The choice of such sequences will be known to those of skill in the art in light of the present disclosure.

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait that one can 'select' for by chemical means, i.e., through the use of a selective agent (e.g., an antibiotic, or the like), or whether it is simply a trait that one can identify through observation or testing, i.e., by 'screening'. Of course, many examples of suitable marker genes are known to the art and can be employed in the practice of the invention.

Included within the terms selectable or screenable marker genes are also genes that encode a "secretable marker" whose secretion can be detected as a means of identifying or selecting for transformed cells. Examples include markers that encode a secretable antigen that can be identified by antibody interaction, or even secretable enzymes that can be detected by their catalytic activity. Secretable proteins fall into a number of classes, including small, diffusible proteins detectable, e.g., by ELISA and small active enzymes detectable in extracellular solution.

Screenable markers that may be employed include, but are not limited to, a β-glucuronidase or uidA gene (GUS) that encode an enzyme for which various chromogenic substrates are known; a beta-lactamase gene (Sutcliffe, 1978), which encodes an enzyme for which various chromogenic substrates are known (e.g., PADAC, a chromogenic cephalosporin); a xylE gene (Zukowsky et al., 1983), which encodes a catechol dioxygenase that can convert chromogenic catechols; an alpha-amylase gene (Ikuta et al., 1990); a tyrosinase gene (Katz et al., 1983) that encodes an enzyme capable of oxidizing tyrosine to DOPA and dopaquinone that in turn condenses to form the easily detectable compound melanin; a beta-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995). Selectable nutritional markers may also be used, such as HIS3, URA3, TRP-1, LYS-2 and ADE2.

Any construct encoding a gene product that results in a recombinant cell useful in biocatalysis may be employed. In one embodiment, the construct encodes an enzyme. Sources of genes for enzymes include those from fungal cells belonging to the genera *Aspergillus, Rhizopus, Trichoderma, Neurospora, Mucor, Penicillium*, yeast belonging to the genera *Kluyveromyces, Saccharomyces, Schizosaccharomyces, Trichosporon, Schwanniomyces*, plants, vertebrates and the like. In one embodiment, the construct is on a plasmid suitable for extrachromosomal replication and maintenance. In another embodiment, two constructs are concurrently or sequentially introduced to a cell so as to result in stable integration of the constructs into the genome.

Enzymes useful in biocatalysis include but are not limited to all six classes of enzymes including hydrolases, lyases, isomerases, ligases, oxidoreductases and transferases, e.g., amidases, alcohol oxidases, carboxylases, dioxygenases, dismutases, demethylases, dehalogenases, dehydrogenases, deaminases, decarboxylases, desulfurases, epoxidases, hydrogenases, hydroxylases, hydratases, kinases, laccases, lactamases, mutases, nitrilases, nitrogenases, oxidases, peroxidases, phosphatases, reductases, racemases, synthetases, thiol oxidases, thiolases, and ureases, and including but not limited to an amylase, aminopeptidase, amyloglucosidase, bromelain, carboxypeptidase, catalase, cellulase, collagenase, esterase, ferulic acid esterase, galactosidase, glucanase, glucoamylase, glucose oxidase, glucosidase, glycolate oxidase, hemicellulase, invertase, lactase, lipase, maltase, papain, pancreatin, pancreatic lipase, pectinase, pectin lyase, pentosanase, pepsin, peptidase, phospholipase A2, polygalacturonase, proteinase, sucrase, trypsin, xylanase, and xylanase. For instance, transketolase and transaminase may be used to prepare chiral amino alcohols, ketones may be converted to secondary alcohols by alcohol dehydrogenase, dentoxifyiline may be converted to lisofylline by alcohol dehydrogenase, and 3-alkyl cyclic ketones may be converted to 4- and 5-substituted lactones by cyclopentanene oxygenase.

In one embodiment, the microbial cells of the invention express 4-hydroxyphenylacetate 3-hydroxylase and in the presence of L-tyrosine, NADH and oxygen, produce L-dihydroxyphenylalanine. In one embodiment, the microbial cells of the invention express glucose, alcohol or formate dehydrogenase and an oxygenase that requires NAD(P) or NAD(P)H. For example, cells that express formate dehydrogenase may be combined with $CO_2$ to produce formic acid; cells that express glucose dehydrogenase may be combined with gluconolactone to produce glucose; cells that express alcohol dehydrogenase may be combined with acetalaldehyde to produce ethanol; and cells that express phosphite dehydrogenase may be combined with phosphite to produce phosphate. In one embodiment, the biocatalytic reaction includes two different enzymes (a "coupled" reaction). In one embodiment, cells that express nitrile hydratase and penicillin G acylase may be employed to produce cephalexin; cells that express alcohol dehydrogenase and $NAD^+$-dependent formate dehydrogenase may be used to produce methyl (R)-3-hydroxybutanoate from methyl acetoacetate; cells that express alcohol or formate dehydrogenase and a monooxygenase may be employed for regio- and stereo-selective biotransformations of lactones (see, e.g., Grogan et al., *Biotech. Lett.*, 14:1125 (1992)). In one embodiment, the cells of the invention express NAD(P)H-flavin oxidoreductase and 4-hydroxyphenylacetate 3-monooxygenase, which are useful in antibiotic biosynthesis.

In one embodiment, microbial cells such as yeast cells, e.g., *Pichia* cells, are spray-dried and employed for production of pyruvate, glyoxylate, resolution of racemic hydroxyacids, and/or production of other keto-acids that glycolate oxidase is capable of oxidizing. In one embodiment, the microbial cells express recombinant glycolate oxidase. Glycolate oxidase includes hydroxy-acid oxidase A and hydroxy-acid oxidase B (L-α-hydroxy acid oxidase, L-2-hydroxy acid oxidase, (S)-2-hydroxy-acid; oxygen 2-oxidoreductase). Glycolate oxidase is a flavoprotein (FMN), and the A form preferentially oxidizes short-chain aliphatic hydroxyl acids, while the B form preferentially oxidizes long-chain and aromatic hydroxyl acids. Glycolate oxidases within the scope of the invention include but are not limited to those from plants, e.g., including but not limited to those from *Solanum, Arabidopsis, Medicago, Fragiara, Spinacia,* and *Hordeum*, or other sources, e.g., from *E. coli, Brucella, Ralsoria, Psuedomonus, Frankia, Bradyrhizobium, Xanthomonas, Synechococcus, Thermosynechochoccus, Gloeobacter, Bacillus, Agrobacterium, Mesorhizobium, Synechocytis, Aspergillus*, or vertebrates including mammals such as bovine, rat, human, mouse and rat.

In one embodiment, the microbial cells, e.g., yeast cells, express recombinant catalase, optionally in addition to recombinant glycolate oxidase. Catalases may exhibit both catalase and peroxidase activity. Catalases within the scope of the invention include but are not limited to catalases from *Saccharomyces, Debaromyces, Yarrowsia,* or *Kluyvermyces*, and those disclosed in NCBI Accession Nos. P83657, CAT1_COMTR; Q9C168, CAT1_NEUCR; P81138, CAT1_PENJA; Q8X182, CAT2_NEUCR; Q9C169, CAT3_NEUCR; Q96528, CATA1_ARATH; Q27487, CATA1_CAEEL; P48350, CATA1_CUCPE; P17598, CATA1_GOSHI; P55307, CATA1_HORVU; P18122, CATA1_MAIZE; P49315, CATA1_NICPL; P00549, CATA1_ORYSI; Q0E4K1, CATA1_ORYSJ; Q01297, CATA1_RICCO; P30264, CATA1_SOLLC; P49284, CATA1_SOLTU; P29756, CATA1_SOYBN; P49319, CATA1_TOBAC; Q43206, CATA1_WHEAT; P25819, CATA2_ARATH; O61235, CATA2_CAEEL; P48351, CATA2_CUCPE; P30567, CATA2_GOSHI; P55308, CATA2_HORVU; P12365, CATA2_MAIZE; P49316, CATA2_NICPL; A2YH64, CATA2_ORYSI; Q0D9C4, CATA2_ORYSJ; P49318, CATA2_RICCO; Q9XHH3, CATA2_SOLLC; P55312, CATA2_SOLTU; P55313, CATA2_WHEAT; Q42547, CATA3_ARATH; P48352, CATA3_CUCPE; P18123, CATA3_MAIZE; P49317, CATA3_NICPL; O48560, CATA3_SOYBN; O48561, CATA4_SOYBN; O28050, CATA_ARCFU; P90682, CAT-A_ASCSU; P78574, CATA_ASPFU; Q9AXH0, CAT-A_AVIMR; P45737, CATA_BACFR; P14412, CAT-A_BACST; P26901, CATA_BACSU; P0A324, CATA_BORBR; P0A325, CATA_BORPA; P0A323, CATA_BORPE; P55304, CATA_BOTCI; P00432, CATA_BOVIN; P0A327, CATA_BRUAB; P0A326, CAT-A_BRUME; Q8FWU0, CATA_BRUSU; Q2I6W4, CATA_CALJA; Q59296, CATA_CAMJE; O13289, CATA_CANAL; Q96VB8, CATA_CANBO; O97492, CATA_CANFA; P07820, CATA_CANTR; Q9M5L6, CATA_CAPAN; O31066, CATA_CAUCR; Q64405, CATA_CAVPO; Q9PT92, CATA_DANRE; Q59337, CATA_DEIRA; Q9ZN99, CATA_DESVM; O77229, CATA_DICDI; P17336, CATA_DROME; P13029, CATA_E-COLI; P55305, CATA_EMENI; Q8X1P0, CATA_ERYGR; P44390, CATA_HAEIN; O59651, CATA_HALMA; O73955, CATA_HALSA; P45739, CATA_HELAN; Q9ZKX5, CATA_HELPJ; P77872, CATA_HELPY; P04040, CATA_HUMAN; P07145, CATA_IPOBA; P30265, CATA_LACSK; Q9WXB9, CATA_LEGPN; Q926X0, CATA_LISIN; Q8Y3P9, CATA_LISMO; P24168, CATA_LISSE; O93662, CATA_METBF; P29422, CATA_MICLU; P24270, CATA_MOUSE; P46817, CATA_MYCBO; O08404, CATA_MYCFO; Q04657, CATA_MYCIT; A0R609, CATA_MYCS2; P00580, CATA_MYCSM; Q08129, CATA_MYCTU; Q59602, CATA_NEIGO; Q27710, CATA_ONCVE; P25890, CATA_PEA; P11934, CATA_PENJA; P32290, CATA_PHAAU; P30263, CATA_PICAN; O62839, CATA_PIG; Q5RF10, CATA_PONPY; P42321, CATA_PROMI; O52762, CATA_PSEAE; Q59714, CATA_PSEPU; Q9PWF7, CATA_RANRU; PO4762, CATA_RAT; P95631, CATA_RHIME; P37743, CATA_RHOCA; Q8Z303, CATA_SALTI; P17750, CATA_SALTY; P55306, CATA_SCHPO; P55310, CATA_SECCE; O24339, CATA_SOLAP; P55311, CATA_SOLME; Q2FH99, CATA_STAA3; Q2FYU7, CATA_STAA8; Q2YXT2, CATA_STAAB; Q5HG86, CATA_STAAC; Q99UE2, CATA STAAM; Q7A5T2, CATA_STAAN; Q6GH72, CATA_STAAR; Q6G9M4, CATA_STAAS; Q9L4S1, CATA_STAAU; Q8NWV5, CATA_STAAW; Q2PUJ9, CATA_STAEP; Q5HPK8, CATA_STAEQ; Q8CPD0, CATA_STAES; Q4L643, CATA_STAHJ; Q49XC1, CATA_STAS1; Q9KW19, CATA_STAWA; Q9EV50, CATA_STAXY; Q9Z598, CATA_STRCO; Q9XZD5, CATA_TOXGO; Q9KRQ1, CATA_VIBCH; O68146, CATA_VIBF1; Q87JE8, CATA_VIBPA; Q8D452, CATA_VIBVU; Q7MFM6, CATA_VIBVY; P15202, CATA_YEAST; Q9X6B0, CATA_YERPE; Q9Y7C2, CATB_AJECA; Q92405, CATB_ASPFU; Q877A8, CATB_ASPOR; P78619, CATB_EMENI; Q59635, CATB_PSEAE; P46206, CATB_PSESY; Q66V81, CATB_STAXY; Q9RJH9, CATB_STRCO; O87864, CATB_STRRE; P30266, CATE_BACPF; P42234, CATE_BACSU; P21179, CATE_ECOLI; P50979, CATE_MYCAV; Q9I1W8, CATE_PSEAE; P95539, CATE_PSEPU; Q9X576, CATE_RHIME; P55303, CATR_ASPNG; P06115, CATT_YEAST; P94377, CATX_BACSU; P80878, MCAT_BACSU; Q97FE0, MCAT_CLOAB; P60355, MCAT_LACPL; Q9LRS0, GOX1_ARATH; Q9LRR9, GOX2_ARATH; P05414, GOX_SPIOL; Q9UJM8, HAOX1_HUMAN; Q9WU19, HAOX1_MOUSE; Q3ZBW2, HAOX2_BOVIN; Q9NYQ3, HAOX2_HUMAN; Q9NYQ2, HAOX2_MOUSE; Q07523, HAOX2_RAT, the disclosures of which are incorporated by reference herein.

In one embodiment, a spray-dried preparation of *Pichia* suitable for biocatalysis is provided. In another embodiment, a spray-dried preparation of *Saccharomyces* suitable for biocatalysis is provided. Nevertheless, as yeast have cell walls, it is envisioned that spray-dried preparations of yeast other than *Pichia* or *Saccharomyces* may be employed for biocatalysis. In one embodiment, the yeast comprises at least one recombinant enzyme. For example, the recombinant enzyme may be a heterologous glycolate oxidase or a heterologous catalase. In one embodiment, the yeast comprises a heterologous glycolate oxidase and a heterologous catalase. In one embodiment, the yeast does not express a recombinant enzyme, e.g., wild-type (or otherwise nonrecombinant) yeast such as *Saccharomyces* may be employed for biocatalysis.

In one embodiment, a spray-dried preparation of prokaryotic cells such as *E. coli* for biocatalysis is provided. For example, a recombinant *E. coli* strain comprises at least one recombinant enzyme. In one embodiment, the *E. coli* strain is transformed with a prokaryotic vector derived from pET32 into which a plant glycolate oxidase open reading frame is inserted.

To prepare recombinant strains of microbes, the microbial genome is augmented or a portion of the genome is replaced with an expression cassette. For biocatalysis, the expression cassette comprises a promoter operably linked to an open reading frame for at least one enzyme that mediates the biocatalysis. For example, the expression cassette may encode a heterologous glycolate oxidase. In one embodiment, the microbial genome is transformed with at least two expression cassettes, e.g., one expression cassette encodes a heterologous glycolate oxidase and another encodes a heterologous catalase. The expression cassettes may be introduced on the same or separate plasmids or the same or different vectors for stable integrative transformation.

Recombinant or native (nonrecombinant) microbes expressing one or more enzymes that mediate a particular enzymatic reaction are expanded to provide a microbial cell suspension. In one embodiment, the suspension may be separated into a liquid fraction and a solid fraction which contains the cells, e.g., by centrifugation or use of a membrane, prior to spray drying. The microbial cell suspension is spray-dried under conditions effective to yield a spray-dried microbial cell preparation suitable for biocatalysis. In one embodiment, the spray drying includes heating an amount of the cell suspension flowing through an aperature. The conditions described in the examples below were set based on small-scale instrument capacity, e.g., low evaporation capacity (e.g., 1.5 Kg water/hour). Thus, the ranges below are exemplary only and may be different at a manufacturing scale where evaporation capacity may reach over 1000 Kg water/hour. For example, for a small scale instrument, the feed (flow) rate may be about 1 mL/minute to about 30 mL/minute, e.g., about 2 mL/minute up to about 20 mL/minute. Flow rates for large scale processes may be up to or greater than 1 L/minute. In one embodiment, the suspension is dried at about 50° C. up to about 225° C., e.g., about 100° C. up to about 200° C. The cell suspension prior to spray drying may be at about 5 mg/L up to about 800 mg/L, for instance, about 20 mg/L up to about 700 mg/L, or up to or greater than 2000 mg/L. The upper limit of the concentration of cells employed is determined by the viscosity of the cells and the instrument. The microbial cell suspension may be an *E. coli* cell suspension, a *Pseudomonas* cell suspension, a *Pichia* cell suspension or a *Saccharomyces* cell suspension. In one embodiment, air flow is about 500 L/hr to about 800 L/hr, e.g., about 700 L/hr. The process to prepare a spray-dried microbial cell preparation may include any flow rate, any temperature and any cell concentration described herein, as well as other flow rates, temperatures and cell concentrations.

Once desirable native or recombinant microbial cells are spray-dried, they may be stored for any period of time under conditions that do not substantially impact the activity or cellular location of enzymes to be employed in biocatalysis. Storage periods include hours, days, weeks, and up to at least 2 months.

In one embodiment, the yeast cells to be spray dried and used in biocatalysis are *Pichia* cells having spinach glycolate oxidase DNA expressed from an Aox1 promoter (single recombinant), or *Pichia* cells having spinach glycolate oxidase DNA and *Saccharomyces* catalase T DNA expressed from Aox1 and Aox2 promoters (double recombinant), which recombinant cells are robust unicellular methylotrophic yeast. Those cells exhibit prokaryotic growth rates, produce the heterologous enzymes intracellularly, have high production rates (grams per liter), have controllable expression (induced by MeOH/repressed by glycerol), and their fermentation is readily scaled up to 100 L. The use of those cells is described below.

The invention will be further described by the following non-limiting examples.

Example 1

Spray-Drying

Equipment

A Buchi B-190 spray-dryer with a pneumatic nozzle cleaner was used for all spray-drying procedures. Controlled operating parameters included: feed concentration, feed rate, air flow, temperature, and vacuum. For all experiments, the air flow was set to 700 L/hour and the vacuum was constant at −50 mbar. Experimental feed concentrations ranged from 30 to 600 mg/mL, feed rates spanned from 5 to 15 mL/minute, and operating temperatures were tested from 120 to 195° C.

Procedure

*Pichia pastoris* cells (designated single or double recombinant) were washed, centrifuged, and stored at −80° C. These cells were obtained from the freezer, allowed to thaw at room temperature, and excess water was removed by blotting the cells on filter paper. The blotted cells were weighed into several containers to yield desired cell concentrations after dilution to a fixed volume. The blotted cells were diluted to 100 mL total volume with deionized water. The containers were agitated, forming cell suspensions at specified concentrations to be used as feeds to the spray-dryer.

Air flow was initiated to the spray-dryer at 700 L/hour, the aspirator was set to −50 mbar, and the heater was powered on. Deionized water was pumped through the spray nozzle in place of the cell suspension. The feed rate was set to the desired experimental value, and the heater was adjusted to yield the correct operating temperature. After reaching temperature equilibrium, the deionized water feed was replaced by the specified cell suspension. The spray-drying process lasted between 6 and 20 minutes based on the feed rate used. When the 100 mL cell suspension had been processed, the feed pump and heater were stopped, and air flow was allowed to cool the machine to 70° C. Then, the aspirator and air supply were shut down. The collection vessel was removed, and the *Pichia* cells were transferred to a scintillation vial. These vials were stored at ambient temperature in a desiccator. The feed line was flushed with deionized water and the glassware rinsed before spray-drying at other conditions.

Enzyme Assays

Glycolate Oxidase Assay

1. Weigh approximately 40 mg spray-dried cells (record exact weight) into a 10 mL centrifuge tube.
2. Add 8.0 mL of DCIP assay solution (0.12 mM 2,6-dichloroindophenol and 80 mM Tris, pH 8.3). A DCIP solution that is stored at 4° C. may be used for up to 2 weeks.
3. Mix to suspend cells, then remove 50 µL of suspension (about 0.25 mg dry cells) and place in 3.0 mL quartz cuvette with flea stirrer. Add 2.0 mL of DCIP assay solution. Cap with septum and bubble with nitrogen for 3 minutes.
4. Add 40 µL of 1.0 M L-lactic acid/1.0 M Tris (pH 8.3) to cuvette by syringe and measure change in absorbance at 606 nm for 30 seconds with stirring ($\epsilon = 22000$ L mol$^{-1}$ cm$^{-1}$).

$$\text{Glycolate oxidase activity (U/g dry cell)} = \frac{(\Delta \text{Abs/min}) * (0.00209 \text{ L}) * (1*10^6 \text{ µmol/mol})}{(22000 \text{ L/mol} * \text{cm}) * (1 \text{ cm}) * (ca\ 0.25 \text{ mg}) * \left(\frac{1 \text{ g}}{1000 \text{ mg}}\right)}$$

Catalase Assay

1. Weigh approximately 40 mg spray-dried cells (record exact weight) into a 10 mL centrifuge tube.
2. Add 8.0 mL of catalase assay buffer (0.0167 M phosphate buffer, pH 7).
3. Mix to suspend cells, then, remove 50 µL of suspension (about 0.25 mg dry cells) and place in a 3.0 mL quartz cuvette with flea stirrer. Add 2.0 mL of catalase assay buffer.
4. Add 1.0 mL of hydrogen peroxide solution (67 µL of 30% peroxide in 10 mL assay buffer, pH 7.0) and measure change in absorbance at 240 nm for 30 seconds with, stirring ($\epsilon = 39.4$ L mol$^{-1}$ cm$^{-1}$).

$$\text{Catalase activity (U/g dry cells)} = \frac{(\Delta \text{Ab/min}) * (0.00305 \text{ L}) * (1*10^6 \text{ µmol/mol})}{(39.4 \text{ L/mol} * \text{cm}) * (1 \text{ cm}) * (ca\ 0.50 \text{ mg}) * \left(\frac{1 \text{ g}}{1000 \text{ mg}}\right)}$$

Experiment #1

This experiment investigated the feasibility of spray-drying transformed *Pichia* cells for glycolate oxidase (GO) and catalase activity, as the temperature shifts associated with the spray-drying process may break-open the *Pichia* cell membranes and rapid moisture loss may stabilize the recombinant enzymes. Single recombinant *Pichia pastoris* (NRRL Y-21001) expressing recombinant GO and native catalase was used. The study was designed to screen feed concentration, feed rate, and operating temperature for their relative effects on GO and catalase activity.

A full-factorial experiment was designed with three factors (feed concentration, feed rate, and operating temperature). A high and low value was investigated for each of the three factors. This resulted in a total of eight experimental runs shown in Table 1.

TABLE 1

| Run | Pattern | Temperature [C.] | Feed Rate [mL/min] | Feed Concentration [mg/mL] |
| --- | --- | --- | --- | --- |
| 601 | − − − | 120 | 5 | 30 |
| 602 | − − + | 120 | 5 | 100 |
| 603 | − + − | 120 | 15 | 30 |
| 604 | − + + | 120 | 15 | 100 |
| 605 | + − − | 150 | 5 | 30 |
| 606 | + − + | 150 | 5 | 100 |
| 607 | + + − | 150 | 15 | 30 |
| 608 | + + + | 150 | 15 | 100 |

GO and catalase enzyme activities were the two responses used to screen these spray-dryer operating parameters. After the spray-dried sample was prepared for enzyme assay, three absorbance measurements were taken.

Software

JMP statistical software (SAS Company) was used to plan the screening experiment and analyze data. The constructed model incorporated feed concentration, feed rate, temperature, and all three interaction parameters (feed concentration*feed rate, feed concentration*temperature, and feed rate*temperature). Standard least squares analysis was used to minimize residual error. Three absorbance measurements for each experimental condition (two replicates) were included in the statistical analysis. Leverage plots are shown to gauge relative influence of the spray-drying parameters on GO and catalase enzyme activity.

Results

Figure 3:
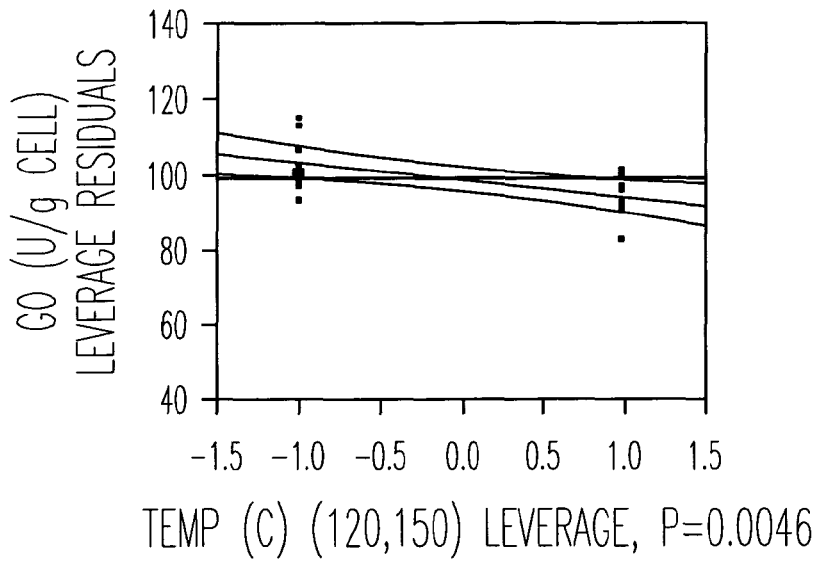
FIG. 3. Glycolate oxidase activity versus temperature.
Figure 4:
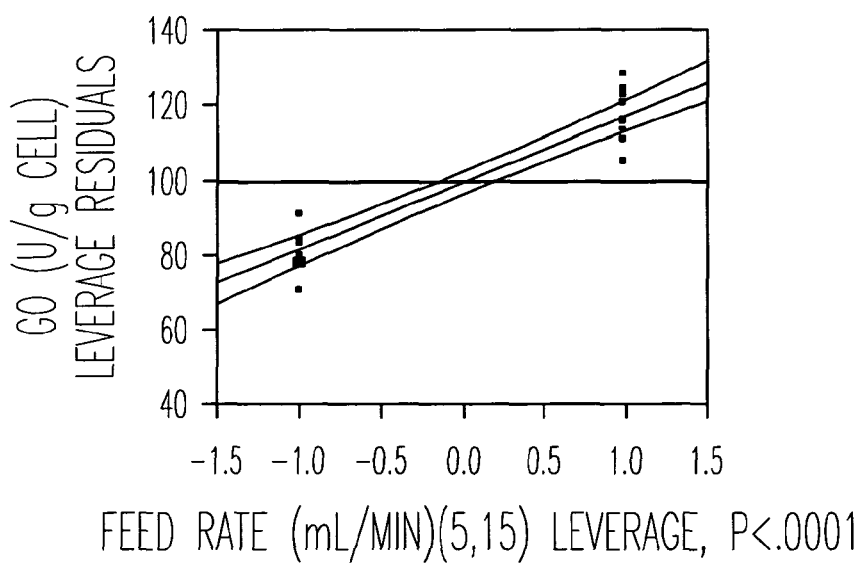
FIG. 4. Glycolate oxidase activity versus feed rate.
Figure 5:
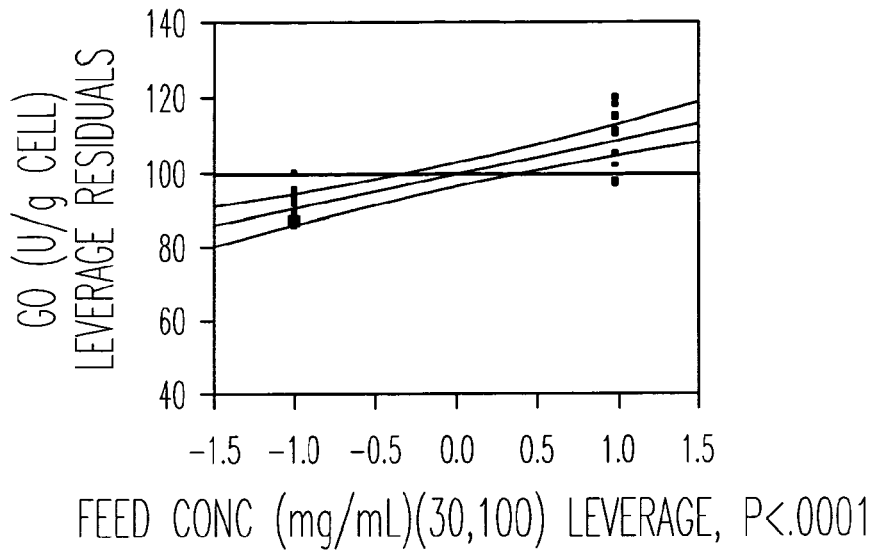
FIG. 5. Glycolate oxidase activity versus feed concentration.
Figure 6:
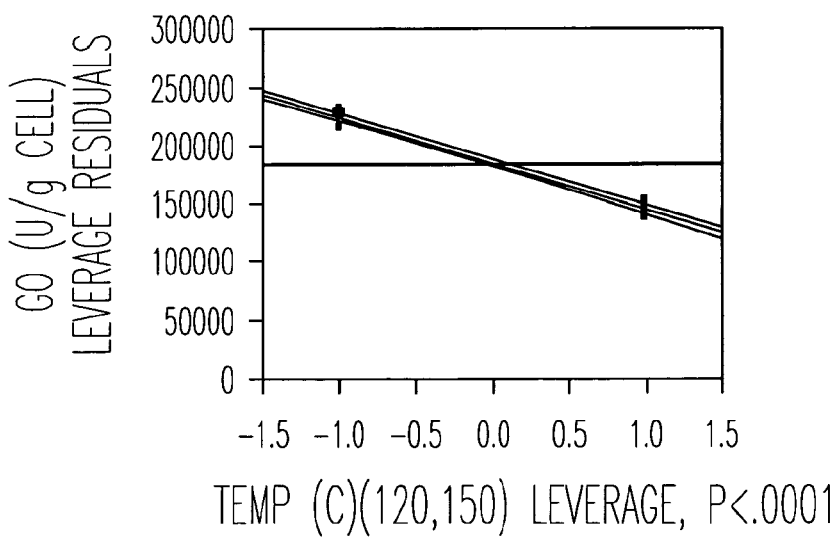
FIG. 6. Catalase activity versus temperature.
Figure 7:
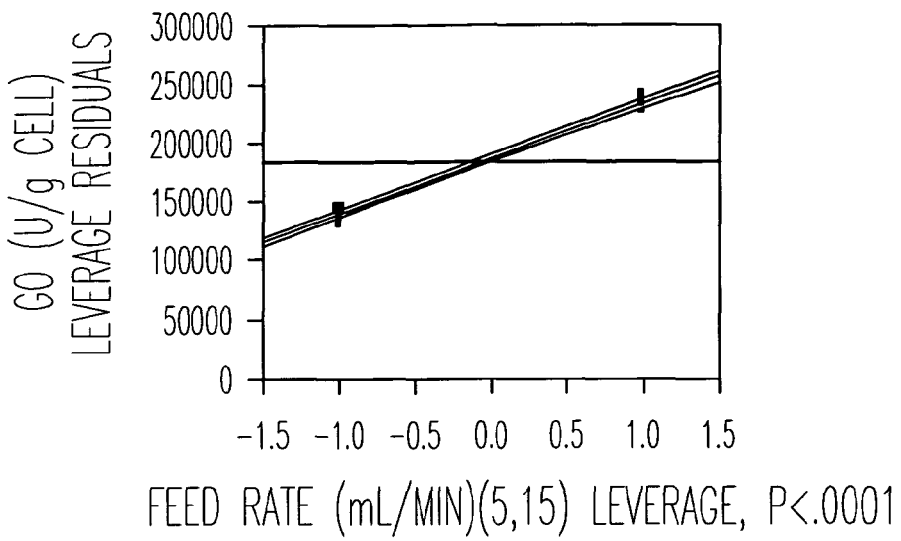
FIG. 7. Catalase activity versus feed rate.
Figure 8:
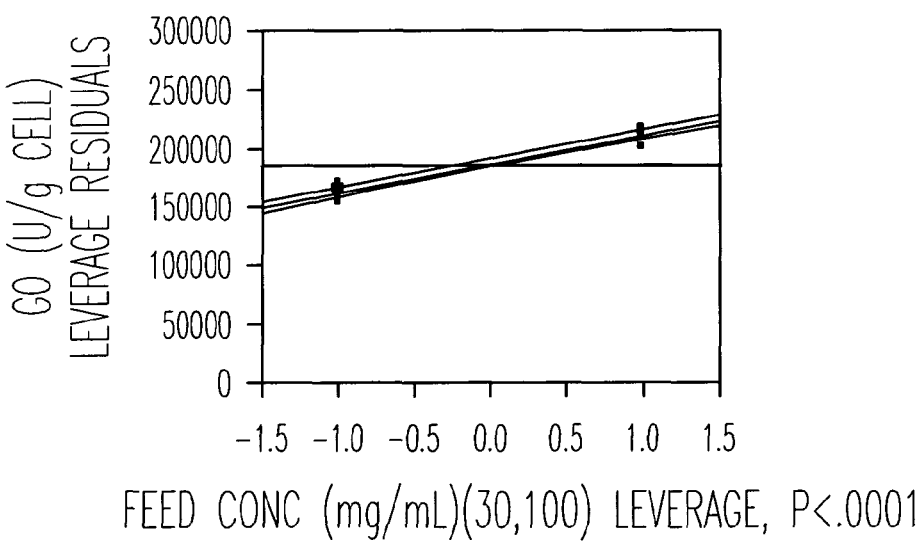
FIG. 8. Catalase activity versus feed concentration.
Figure 9:
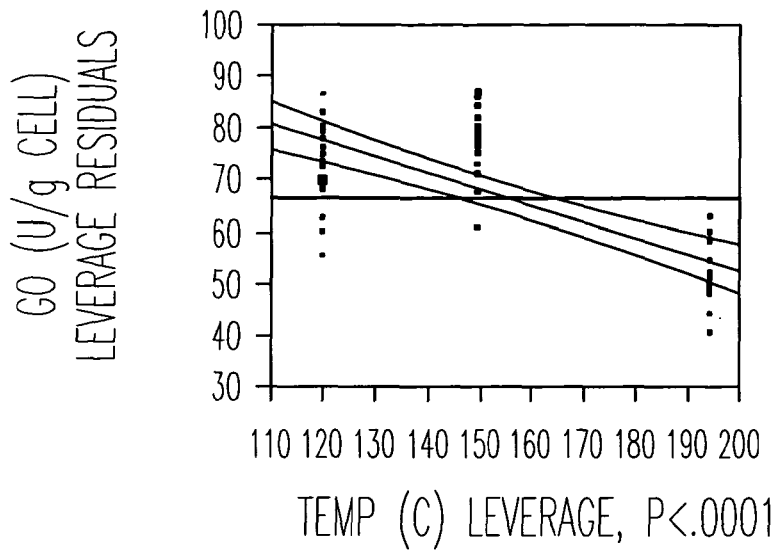
FIG. 9. Glycolate oxidase activity versus temperature.
Figure 10:
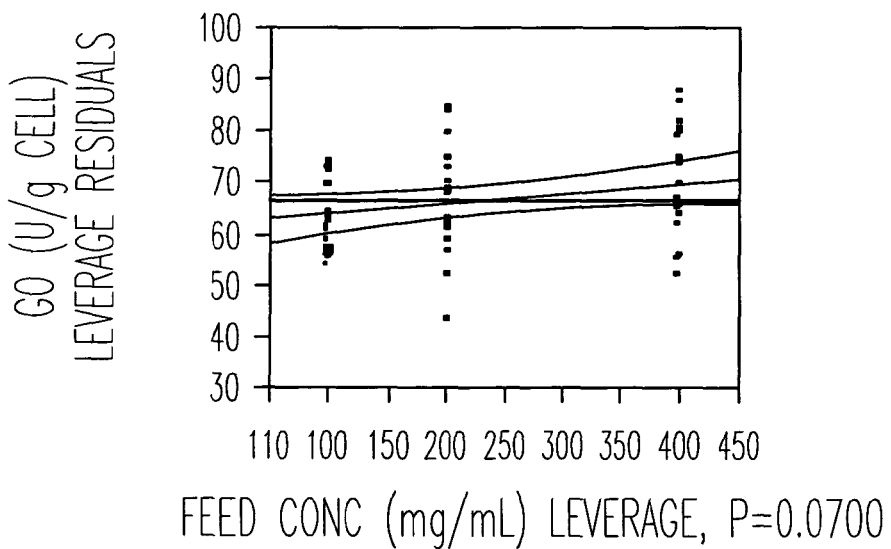
FIG. 10. Glycolate oxidase activity versus feed concentration.
Figure 11:
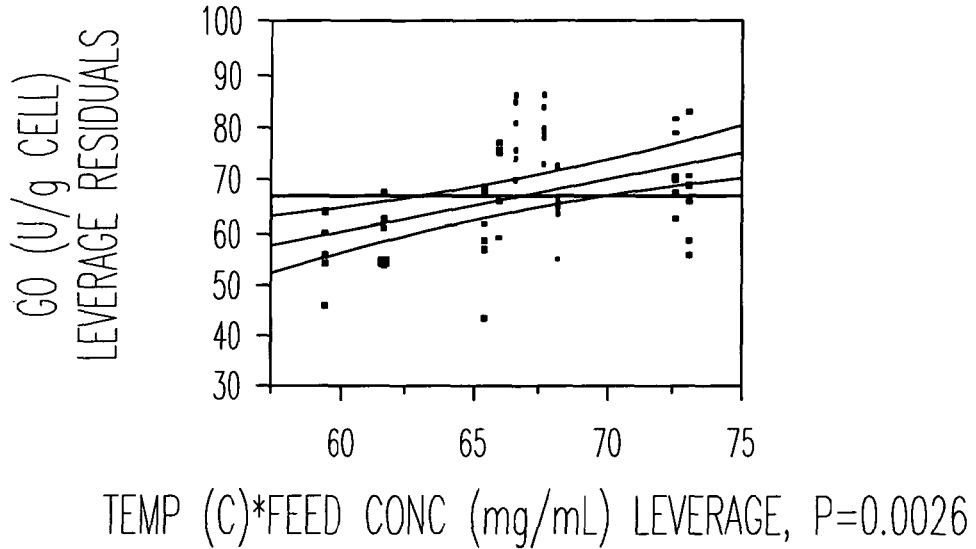
FIG. 11. Glycolate oxidase activity versus temperature*feed concentration.
Figure 12:
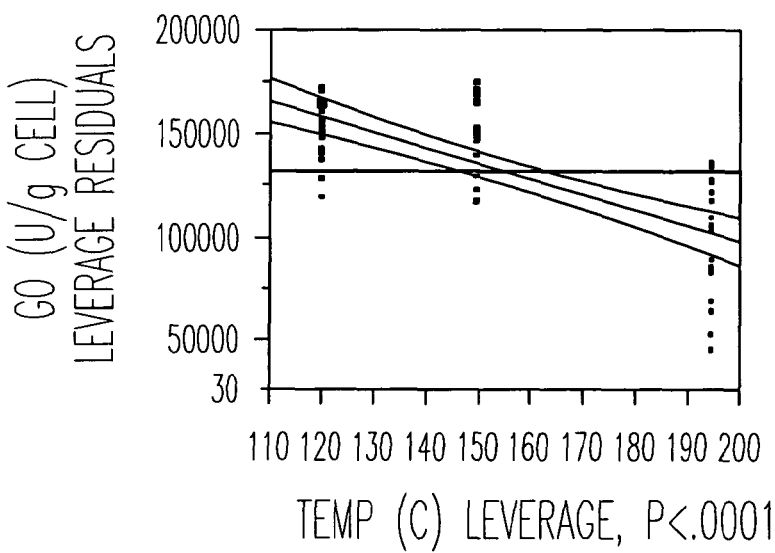
FIG. 12. Catalase activity versus temperature.
Figure 13:
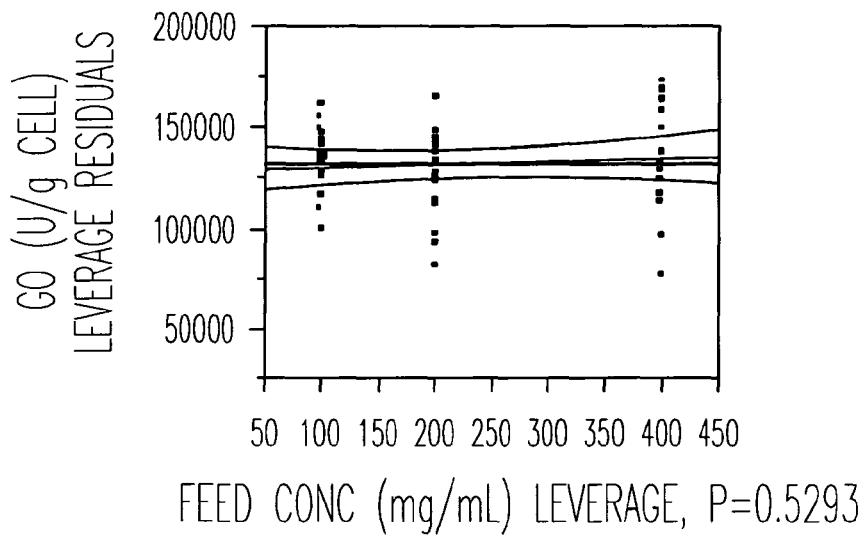
FIG. 13. Catalase activity versus feed concentration.
Figure 14:
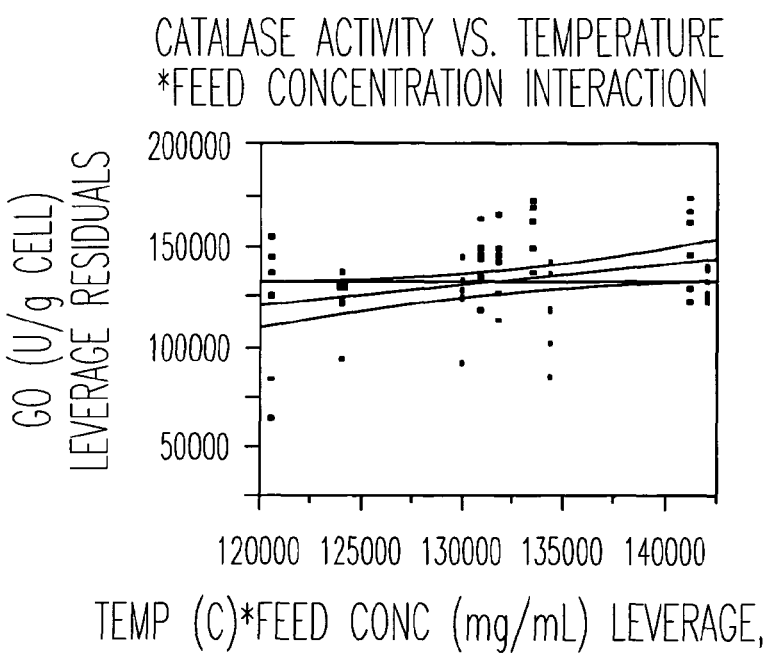
FIG. 14. Catalase activity versus temperature*feed concentration.

All three spray-dryer operating parameters were significant for GO activity shown by the 95% confidence intervals crossing the horizontal axes. Increasing the temperature from 120 to 150° C. had a slight negative effect on GO activity, while increasing the feed rate from 5 to 15 mL/minute had the steepest leverage slope and the most significant effect on GO activity (FIGS. 3-4). Increasing the feed concentration from 30 to 100 mg/mL also raised GO activity (FIG. 5). The temperature*feed rate interaction plot (not shown) suggested that increasing the feed rate would minimize GO activity loss incurred when spray-drying at higher temperatures.

The spray-dryer operating parameters were also significant for catalase activity. Increasing the temperature from 120 to 150° C. had a more drastic decrease on catalase activity compared to GO activity (FIG. 6). Consistent with GO results, increasing the feed rate from 5 to 15 mL/minute had the greatest impact on catalase activity (FIG. 7). Elevating the feed concentration from 30 to 100 mg/mL raised catalase activity (FIG. 8). The temperature*feed rate and temperature*feed concentration interaction plots (not shown) suggested that increasing the feed rate and feed concentration would minimize the catalase activity loss from spray-drying at higher temperatures.

Experiment #2

After demonstrating feasibility of spray-drying transformed *Pichia* cells for biocatalysis, a second experiment focused on increasing GO and catalase enzyme activity. When considering results from experiment #1 for both enzymes: a) increasing temperature showed a decrease in activity, b) elevating feed rate had the greatest positive effect on activity, and c) increasing feed concentration raised activity. Based on these results, the feed rate was set to 15 mL/minute (instrument maximum) for the second experiment. Lower temperatures were not investigated because spray-drying at 120° C. produced a "caked" powder (due to residual moisture) when operating at higher feed rates. As an alternative, higher feed concentrations were studied to retain enzyme activity when spray-drying above 120° C. Double recombinant *Pichia pastoris* expressing GO, native catalase, and catalase T from *Saccharomyces cerevisiae* was used.

A full factorial experiment was designed with two factors (temperature and feed concentration). Three different temperatures and three different feed concentrations were tested. This resulted in a total of nine experimental runs shown in Table 2.

TABLE 2

| Run | Pattern | Temperature [C.] | Feed Concentration [mg/mL] |
|---|---|---|---|
| 702 | 11 | 120 | 100 |
| 703 | 12 | 120 | 200 |
| 704 | 13 | 120 | 400 |
| 705 | 21 | 150 | 100 |
| 706 | 22 | 150 | 200 |
| 707 | 23 | 150 | 400 |
| 708 | 31 | 195 | 100 |
| 709 | 32 | 195 | 200 |
| 710 | 33 | 195 | 400 |

Again, GO and catalase enzyme activities were the two responses used to screen these spray-dryer operating parameters. After the spray-dried sample was prepared for enzyme assay, six absorbance measurements were completed.

JMP statistical software was used to develop a model based on temperature, feed concentration, and one interaction parameter (temperature*feed concentration). Run 702 (120° C., 100 mg/mL) and run 705 (150° C., 100 mg/mL) were operating parameters repeated from the first experiment. Higher feed concentrations and higher operating temperatures were tested. The maximum controlled temperature (at the specified feed rate) was 195° C. This upper temperature limit was studied to enhance results from increasing the feed concentration and to determine a temperature optimum. Six absorbance measurements for each experimental condition (5 replicates) were included in the statistical analysis. Leverage plots are shown for GO and catalase enzyme activity vs. the spray-drying parameters.

Results

For the second experiment, spray-drying at 195° C. resulted in significantly lower GO activity compared to the 120 and 150° C. conditions (FIG. 9). The benefit of spray-drying at higher feed concentrations is not evident by observing the feed concentration leverage plot (FIG. 10). The 95% confidence interval does not cross the horizontal axis, and increasing the feed concentration does not show a statistically significant change in GO activity. However, there are two benefits to increasing the feed concentration: a) more *P. pastoris* cells can be processed per unit volume, and b) the temperature*feed concentration interaction plot shows higher feed concentrations helped achieve comparable GO activity for the 120 and 150° C. runs (FIG. 11). These results are important because spray-drying at 150° C. yields a more uniform biocatalyst powder with less residual moisture than operating at 120° C.

Following GO results, spray-drying at 195° C. significantly decreased catalase activity compared to lower operating temperatures (FIG. 12). Spray-drying at 120 and 150° C. yielded comparable catalase activity. Increasing the feed concentration provided no statistical change in catalase activity, demonstrated by the feed concentration plot and the temperature*feed concentration interaction plot (FIGS. 13-14). The catalase enzyme did not receive the same benefit as GO when spray-dried at higher feed concentrations. Catalase could be more resilient to temperature increases from 120 to 150° C., and therefore not need higher feed concentrations to maintain enzyme activity. Spray-drying *P. pastoris* cells up to 400 mg cells/mL (wet cell weight) can be accomplished without loss in GO or catalase activity.

Experiment #3

The first experiment demonstrated that increasing feed rate retained GO and catalase enzyme activity in spray-dried cells. The feed rate was set to the instrument maximum (15 mL/minute) for experiment #2 where higher temperatures and feed concentrations were tested. Temperatures of 120 and 150° C. yielded similar enzyme activities, but the 150° C. condition gave a more uniform and dry biocatalyst powder. The maximum operating temperature of 195° C. was studied, and clearly, there exists an upper temperature limit for best enzyme activity. An upper limit on feed concentration could not be determined from the second experiment where feeds up to 400 mg/mL were tested without any statistical change in enzyme activity.

For the third experiment, the best feed rate (15 mL/minute) and best temperature (150° C.) from previous studies were used. Increasing feed concentration can be beneficial by reducing processing volume and helping maintain enzyme activity if spray-drying at temperatures above 150° C. was used. Feed concentrations of 200 and 400 mg/mL were repeated and 600 mg/mL was also investigated. The viscosity of the 600 mg/mL concentration slowed the feed rate to 13 mL/minute. Concentrations above 600 mg/mL were not tested because earlier experiments proved high feed rates yielded better enzyme activities than increasing feed concentration. Table 3 below is a summary of conditions for experiment #3.

TABLE 3

| Run | Feed Concentration [mg/mL |
|---|---|
| 712 | 200 |
| 713 | 400 |
| 714 | 600 |

Further Studies

Enzyme stability studies, cell permeabilization studies, enzyme leaching studies, and enantiomeric specificity studies were also investigated.

Enzyme Stability.

The spray-dried cells were stored at room temperature in a desiccator (to prevent moisture contamination). These cells were assayed for enzyme activity over a 17-day period to observe possible activity loss and quantify enzyme stability.

Cell Permeabilization.

In initial work (in the absence of spray-drying), after fermentation, cells were recovered by solid/liquid separation, and benzalkonium chloride (BAC) detergent was used to permeabilize cells for the enzyme reaction. Nevertheless, the results from experiment #1 hereinabove showed the feasibility of using spray-dried cells for GO and catalase activity. Thus, another experiment (see below) compared spray-dried cells to several other methods of cell preparation: a) not spray-dried and not BAC treated, b) not spray-dried and treated with BAC, and c) spray-dried and treated with BAC. The spray-dried cells were treated with BAC after spray-drying to determine if spray-drying completely permeabilized the cells.

Enzyme Leaching.

It is beneficial to have GO and catalase contained within the whole cell biocatalyst. The cells offer protection from shear forces in the reactor, keep the enzymes spatially close so they can work together, and facilitate enzyme recovery for reuse. For these reasons, leaching of GO and catalase from spray-dried cells was investigated.

Methods

Detergent Cell Permeabilization

1. Prepare mixture of 10 weight % cells/volume 50 mM phosphate buffer (pH 7.0) at room temperature. Add 0.1% (w/v) benzalkonium chloride.
2. Stir or mix slowly for 60 minutes at room temperature, 25° C.
3. Centrifuge (9950×g for 10 minutes at 5° C.), decant, and re-suspend cells three times (10% w/v) in 50 mM phosphate buffer (pH 7.0) at 5° C., centrifuge, decant.
4. Permeabilized cells may be used immediately or stored up to one year at −80° C. prior to use.

Glycolate Oxidase Leaching Assay

1. Weigh approximately 40 mg spray-dried cells (record exact weight) into a 10 mL centrifuge tube.
2. Add 8.0 mL of DCIP assay solution (0.12 mM 2,6-dichloroindophenol and 80 mM Tris, pH 8.3).
3. Mix to suspend cells, then remove 50 µL of suspension (about 0.25 mg dry cells) and place in 3.0 mL quartz cuvette with flea stirrer. Add 2.0 mL of DCIP assay solution. Cap with septum and bubble with nitrogen for 3 minutes.
   * When testing supernatant (for enzyme leaching), use 2.05 mL of supernatant and do not dilute further with assay buffer.
4. Add 40 µL of 1.0 M glycolic acid (or L-lactic acid)/1.0 M Tris (pH 8.3) to cuvette by syringe and measure change in absorbance at 606 nm for 30 seconds with stirring ($\epsilon = 22000$ L mol$^{-1}$ cm$^{-1}$).
5. Calculate the total glycolate oxidase activity.
6. Centrifuge cell suspension at 9950×g for 10 minutes. Measure enzyme activity of supernatant (without buffer dilution).
7. Re-suspend cell pellet in 6.0 mL assay buffer and repeat enzyme assay on cell suspension and supernatant.

Catalase Leaching Assay

1. Weigh approximately 40 mg spray-dried cells (record exact weight) into a 10 mL centrifuge tube.
2. Add 8.0 mL of catalase assay buffer (0.0167 M phosphate buffer, pH 7).
3. Mix to suspend cells, then remove 50 µL of suspension (about 0.25 mg dry cells) and place in a 3.0 mL quartz cuvette with flea stirrer. Add 2.0 mL of catalase assay buffer.
   * When testing supernatant (for enzyme leaching), use 2.05 mL of supernatant and do not dilute further with assay buffer.
4. Add 1.0 mL of hydrogen peroxide solution (67 µL of 30% peroxide in 10 mL assay buffer, pH 7.0) and measure change in absorbance at 240 nm for 30 s with stirring ($\epsilon = 39.4$ L mol$^{-1}$ cm$^{-1}$).
5. Calculate the total catalase activity.
6. Centrifuge cell suspension at 9950 g for 10 minutes. Measure enzyme activity of supernatant (without buffer dilution).
7. Re-suspend cell pellet in 6.0 mL assay buffer and repeat enzyme assay on cell suspension and supernatant.

Results

Enzyme Activity

Figure 15:
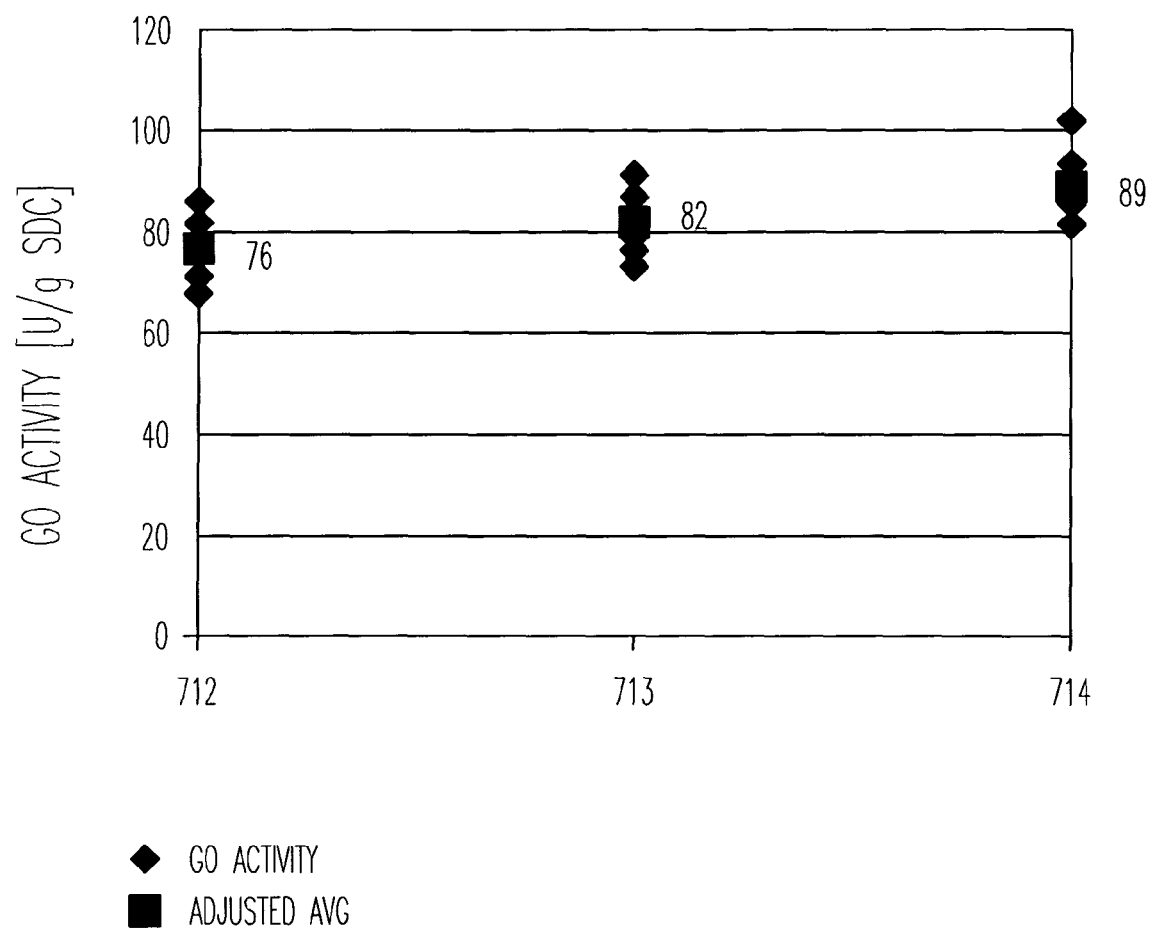
FIG. 15. Glycolate oxidase activity in spray-dried yeast cells.
Figure 16:
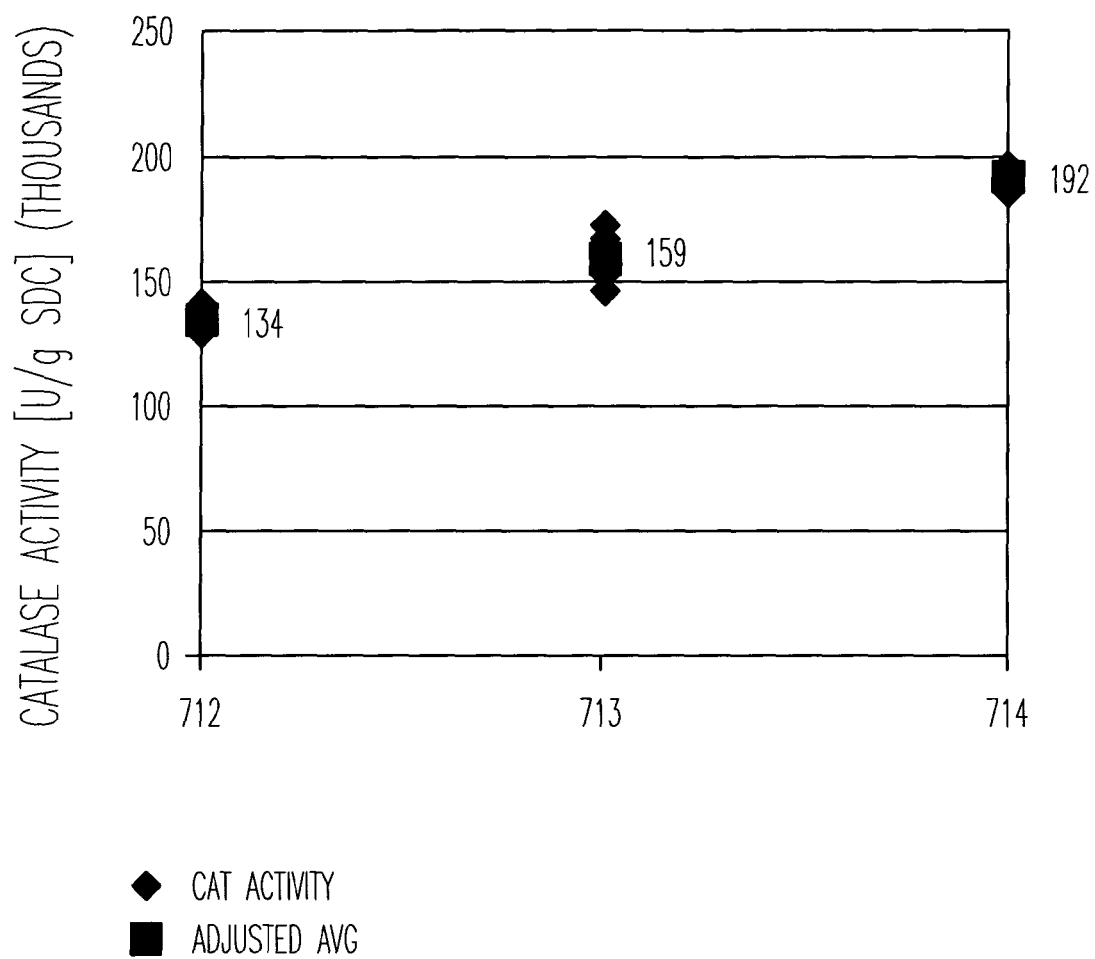
FIG. 16. Catalase activity in spray-dried yeast cells.

The feed rate was held constant at 15 mL/minute and temperature was set to 150° C. Conditions 712, 713, and 714 had feed concentrations of 200, 400, and 600 mg cells/mL, respectively. Six absorbance measurements (5 replicates) were taken for each condition and used to calculate enzyme activities. The six enzyme activities were plotted along with an adjusted average. The adjusted average is an average of the four middle enzyme activities (dropping the highest and lowest numbers). All three conditions tested had overlapping GO activities, but the adjusted averages increased slightly with each successive feed concentration (FIG. 15). The catalase assay showed less variability, and the 600 mg/mL condition clearly had the highest resulting catalase activity (FIG. 16).

Feed concentrations up to 600 mg/mL were spray-dried resulting in high enzyme activities and low processing volumes. Higher feed concentrations were not studied because their viscosities decreased feed rates below the 15 mL/minute optimum.

Enzyme Stability

Figure 17:
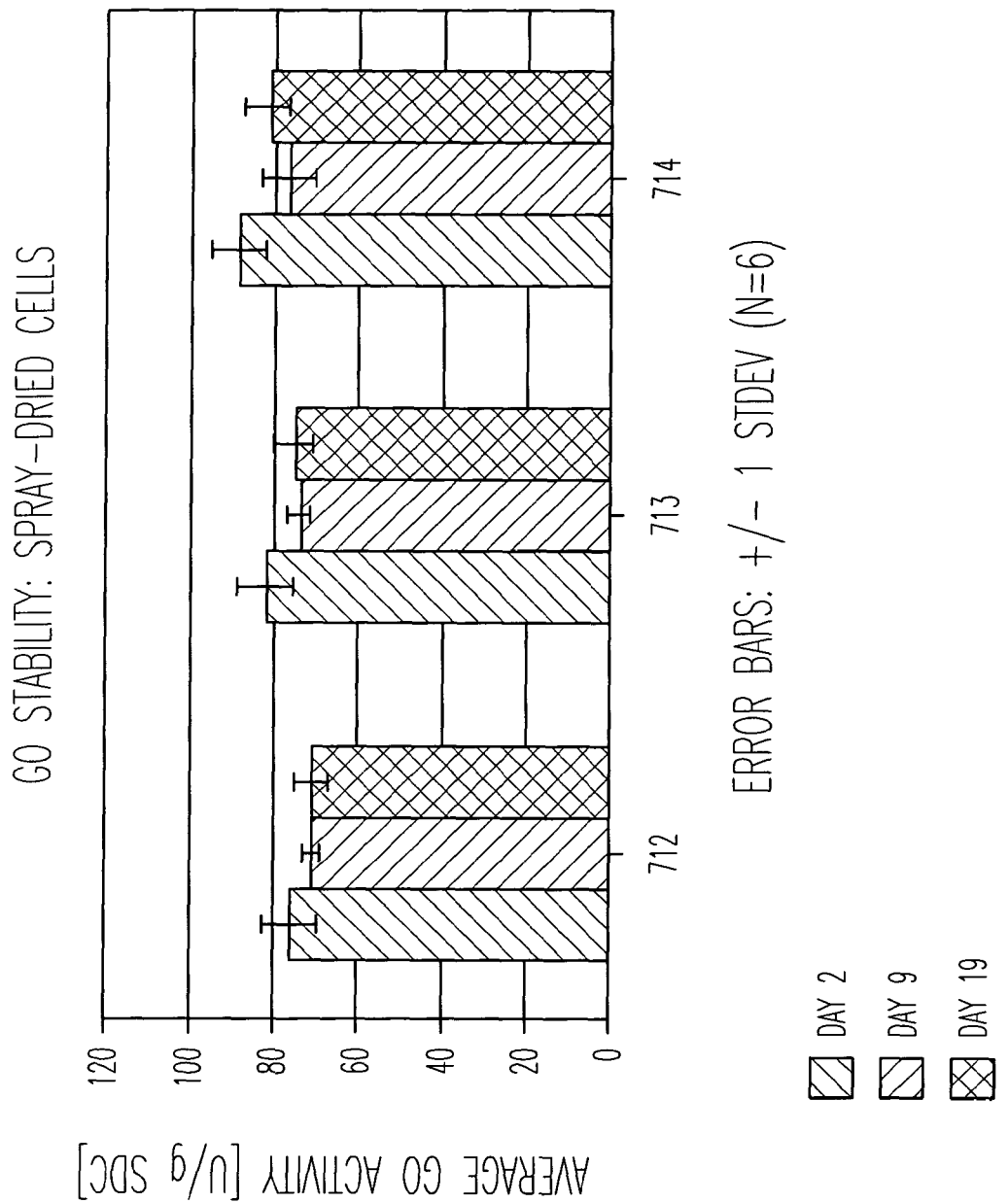
FIG. 17. Glycolate oxidase stability in spray-dried yeast cells.
Figure 18:
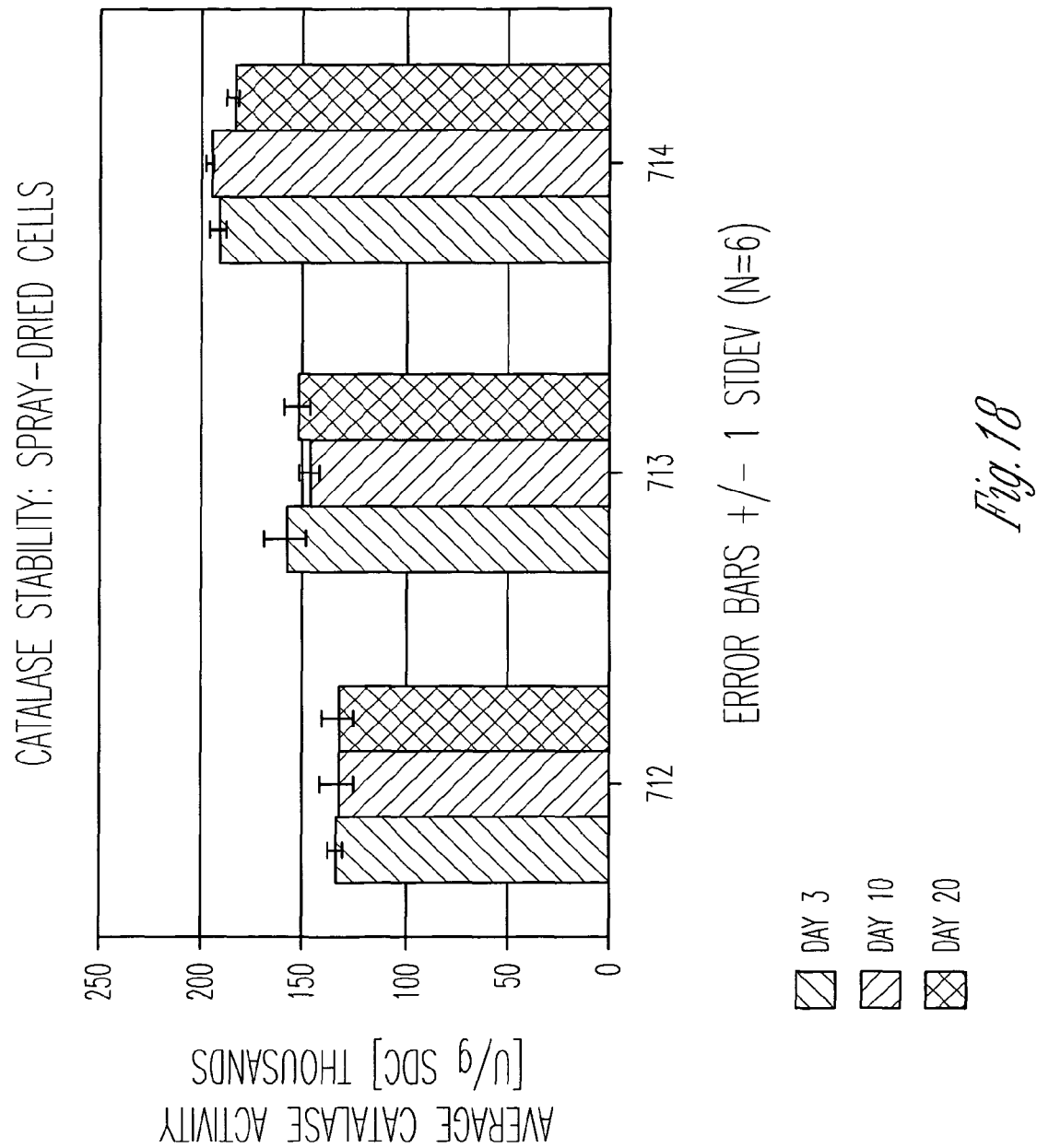
FIG. 18. Catalase stability in spray-dried yeast cells.

Initial work used BAC detergent to permeabilize cells instead of spray-drying, and BAC treated cells required storage at −80° C. to maintain enzyme activity. Spray-dried cells were stored in a desiccator at room temperature. The spray-dried cells were sampled for enzyme activity three times over a 17-day period. For each sampled condition, six absorbance measurements were taken. The average value was plotted with error bars signifying one standard deviation. Considering GO and catalase, no statistical loss in activity was observed over the 17-day sampling period (FIGS. 17-18).

Cell Permeabilization

Figure 19:
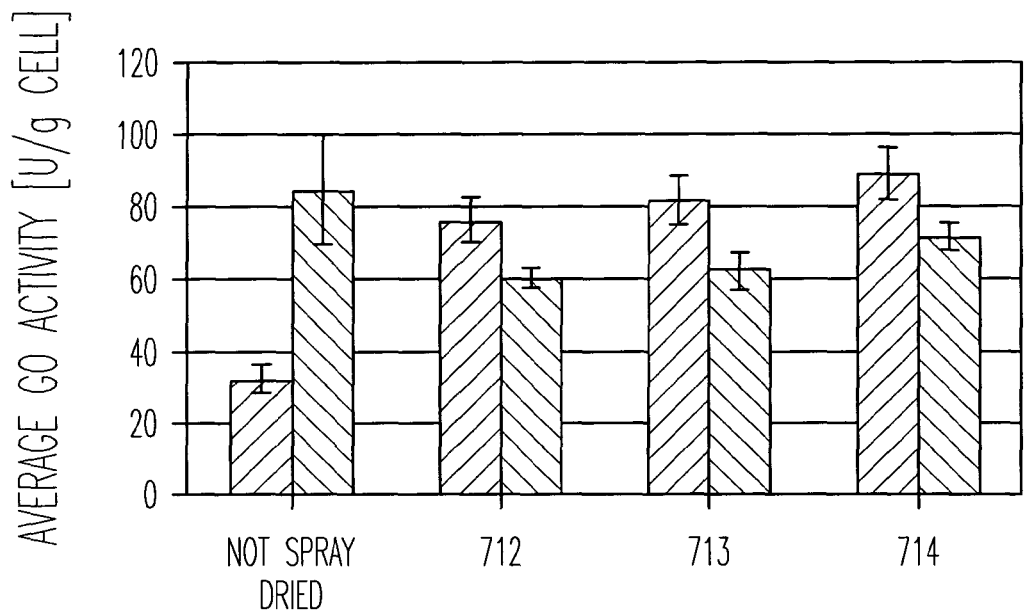
FIG. 19. Glycolate oxidase activity in spray-dried yeast cells that have been detergent permeabilized.
Figure 20:
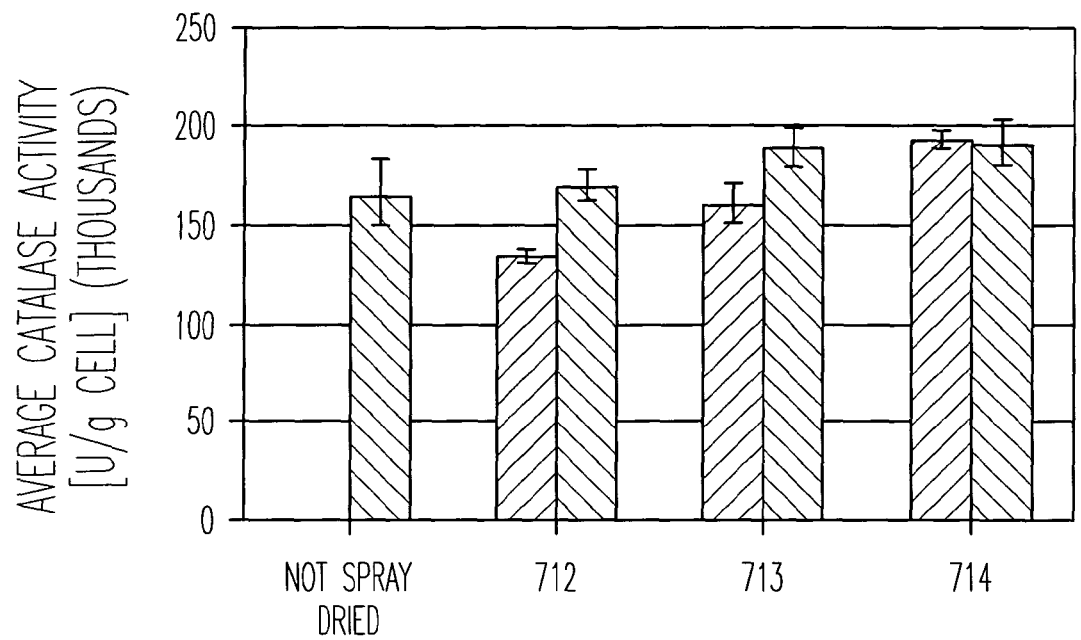
FIG. 20. Catalase activity in spray-dried yeast cells that have been detergent permeabilized.

The current method of spray-drying cells for enzyme activity was compared to initial work using BAC detergent permeabilization. Again, each condition had six absorbance measurements. The average was plotted, and error bars show one standard deviation. All BAC treated cells were permeabilized and washed according to "BAC Detergent Permeabilization." Because BAC treatment involves phosphate buffer, all permeabilized cells were assayed using 40 mg blotted (wet) cells. Spray-dried cells that had not been permeabilized were assayed using 40 mg dry cell weight, and so had more enzyme per given cell mass. While a direct comparison between permeabilized cells and spray-dried cells cannot be made, two important conclusions can be understood. Cells that had not been spray-dried required BAC permeabilization to reach useful levels of GO and catalase enzyme activity, but all spray-dried cells had appreciable levels of enzyme activity without added detergent (FIGS. 19-20). Second, cells that were permeabilized post spray-drying showed lower GO activity but gave comparable/higher catalase activity meaning BAC detergent could be toxic to the GO enzyme.

TABLE 4

Effect of benzalkonium chloride on the GO activity of post spray-dried (SD) pichia pastoris

| BAC concentration | Average GO activity in IU/g spray-dried cells | | |
|---|---|---|---|
| (w/v) | Lactic acid | 3-Ph-lactic acid | 2-OH-butyric acid |
| SD cells* | 132 | 34 | 146 |
| 0% BAC | 139 | 39 | 162 |
| 0.02% BAC | 143 | 36 | 162 |
| 0.1% BAC | 149 | 35 | 185 |

*These assays were done with 4 days old DCIP assay solution

Leaching

Figure 21:
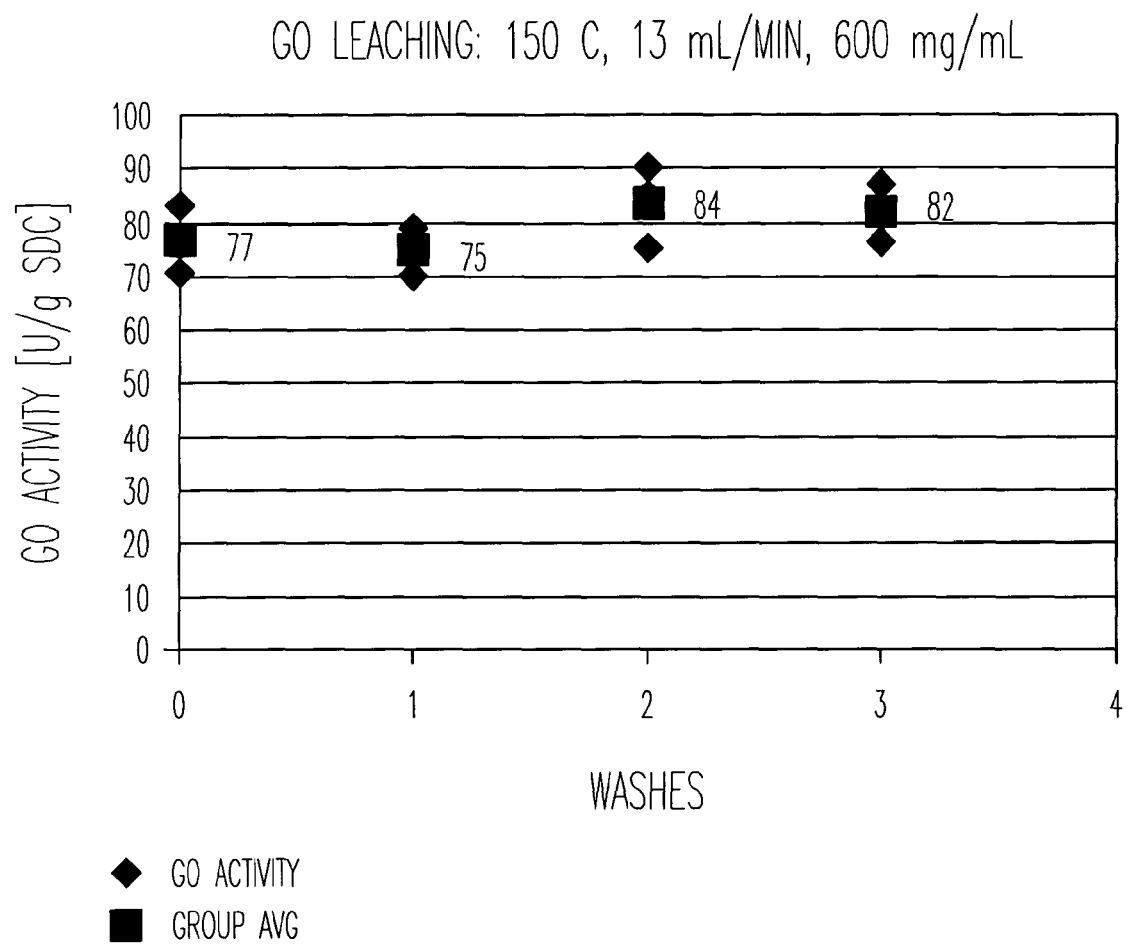
FIG. 21. Testing for the presence or absence of glycolate oxidase leaching from spray-dried yeast cells.
Figure 22:
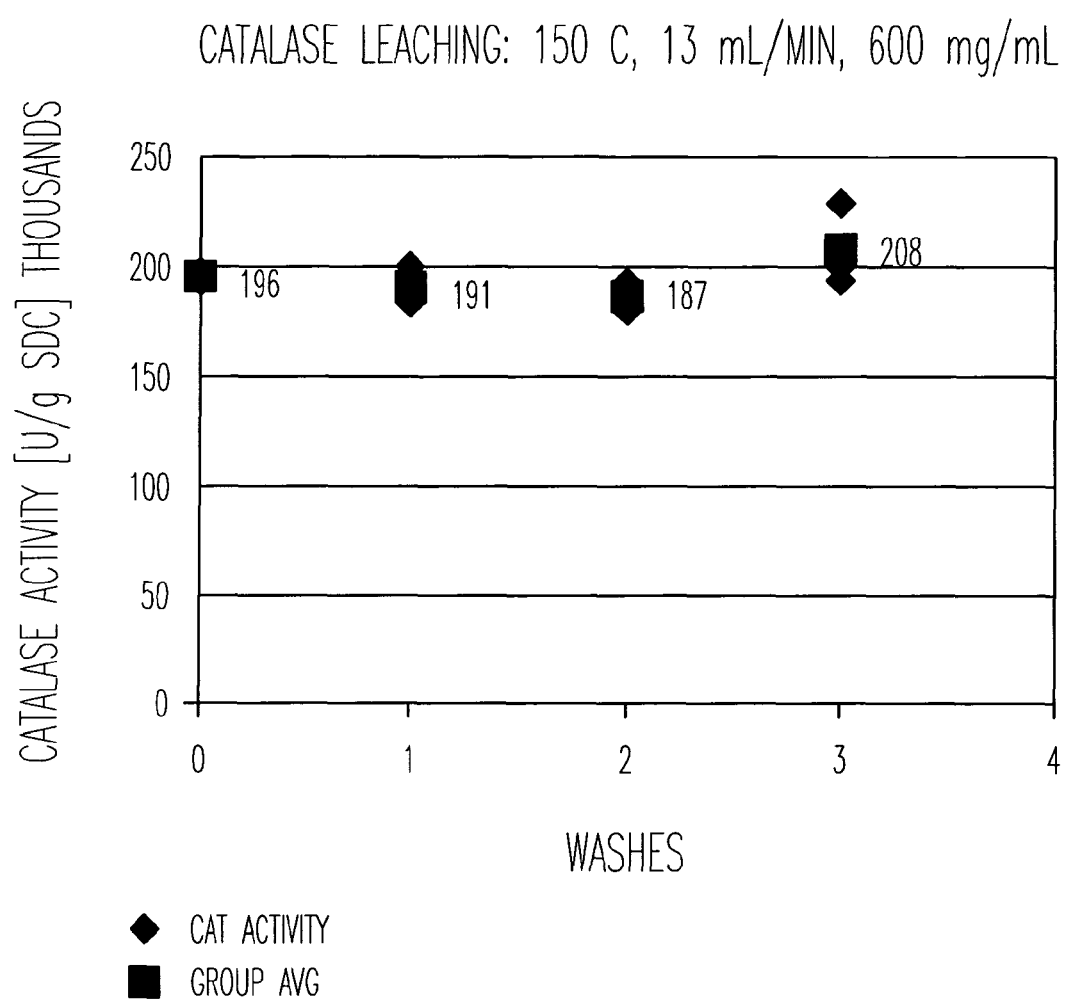
FIG. 22. Testing for the presence or absence of catalase leaching from spray-dried yeast cells.

Operating conditions to study leaching were 150° C., 600 mg cells/mL, and 13 mL/minute (low feed rate due to high feed viscosity). Three absorbance readings were taken, resulting enzyme activities were plotted, and the group average or statistical mean was shown. This process was repeated after three separate washings and the cell suspension and wash supernatant were tested for enzyme activity. Plots of enzyme activity for the cell suspension are shown in FIGS. 21-22. No statistical change in GO or catalase enzyme activity was observed after each of the three washings. Furthermore, no measurable enzyme activity was detected in the wash supernatant (not shown). This is a strong indication that spray-dried cells will not leach GO and catalase enzymes and can be recycled through the enzyme reaction environment.

Specificity

Figure 23:
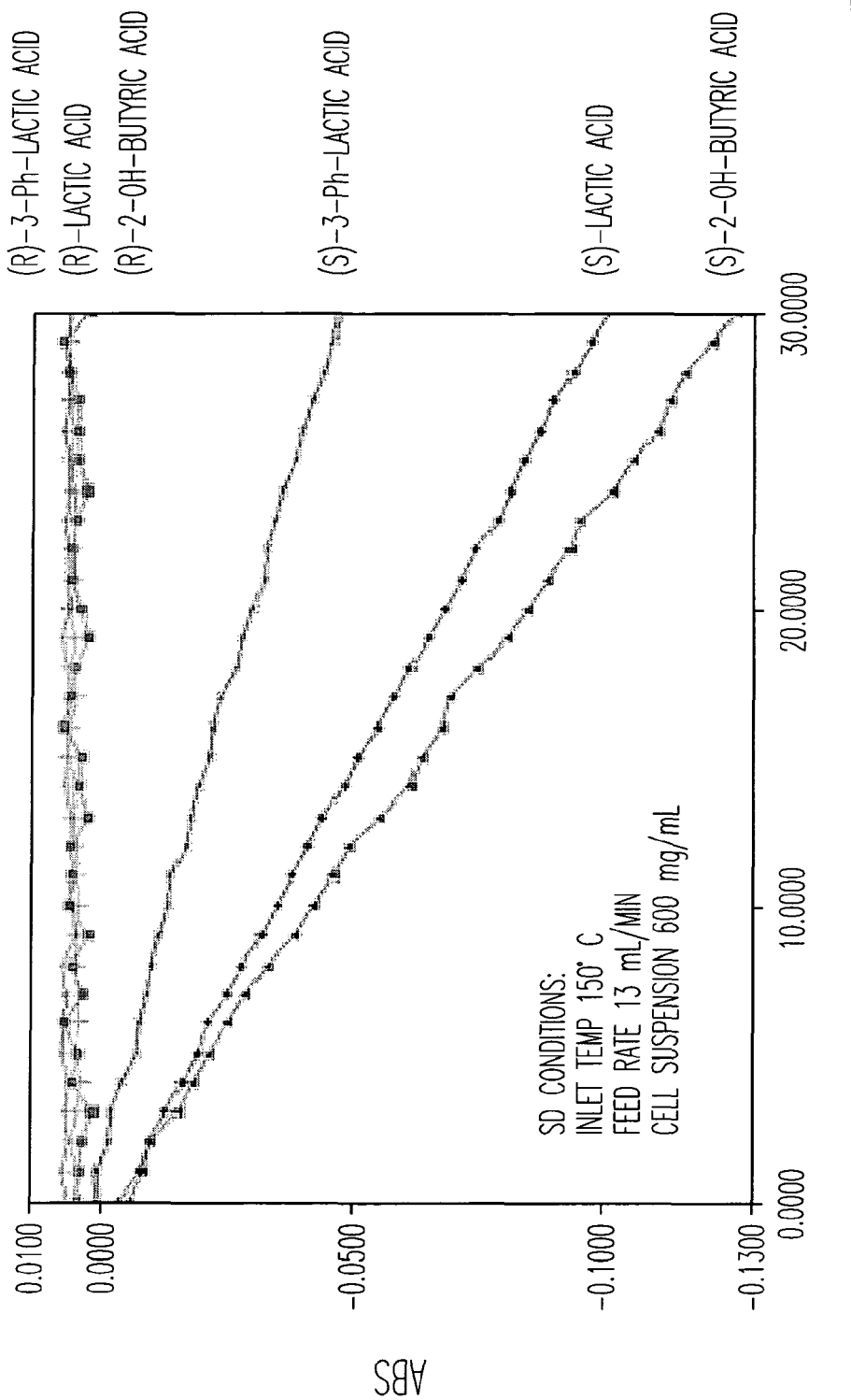
FIG. 23. Enantiomeric specificity of spray-dried yeast cells with glycolate oxidase and catalase.

The specificity of glycolate oxidase for various substrates and enantiomers is shown in Table 5 and FIG. 23.

TABLE 5

Comparison of relative GO activities where lactic acid is 100%

| Racemic 2-hydroxy- carboxylic acids | Relative activity in % | |
|---|---|---|
| | Permeabilized | Spray-dried |
| Lactic acid | 100 | 100 |
| 3-Indolelactic acid | 18 | 26 |
| 3-Phenyllactic acid | 25 | 37 |
| p-Hydroxyphenyllactic acid | 26 | 38 |
| β-Chlorolactic acid | 100 | 121 |
| Trifluorolactic acid | 11 | 2 |
| 2-Hydroxybutyric acid | 91 | 129 |
| 2-Hydroxy-3-methylbutyric acid | 1 | 2 |
| Glycolic acid | 90 | 94 |
| Mandelic acid | 3 | 3 |
| 2-Hydroxydecanoic acid | 40 | 49 |

In summary, spray drying of *Pichia* cells renders it porous for biocatalysis, without the need for any enzyme purification or processing. Moreover, maximum activity is achieved with many substrates without treatment with porosity agents, the spray-dried cells and enzymes are stable for up to 30 days at room temperature. Further, the reaction is fully enantioselective with respect to glycolate oxidase.

Example 2

Expression of GO in *E. Coli*

The GO gene was cloned into the *E. coli* expression plasmid pET-32a (Novagen). A forward PCR primer (GO-AseI-F, 5'GGCTCGG<u>ATTAAT</u>GGAGATCACAAATGTGAACG-3; SEQ ID NO:1) and a reverse PCR primer (GO-XhoI-R, 5'-GCATGC<u>CTCGAG</u>TTATAATCTGGCAACAGCACG-3; SEQ ID NO:2) were used for PCR amplification of the GO gene from plasmid pPM1 (Payne et al., *Gene*, 167:215 (1995)). The 1.1 kb PCR product was first digested with AseI and XhoI and subsequently ligated with a 5.4 kb fragment of pET-32a obtained from a NdeI-XhoI digestion. The resultant recombinant plasmid was named as pET-GO#11. DNA sequencing of pET-GO#11 showed that the cloned GO gene had a single point mutation (probably resulted from PCR amplification) which did not alter the GO protein sequence. Therefore, pET-GO#11 was transformed into *E. coli* Rosetta-gami B(DE3) cells (Novagen) for protein expression.

Figure 24:
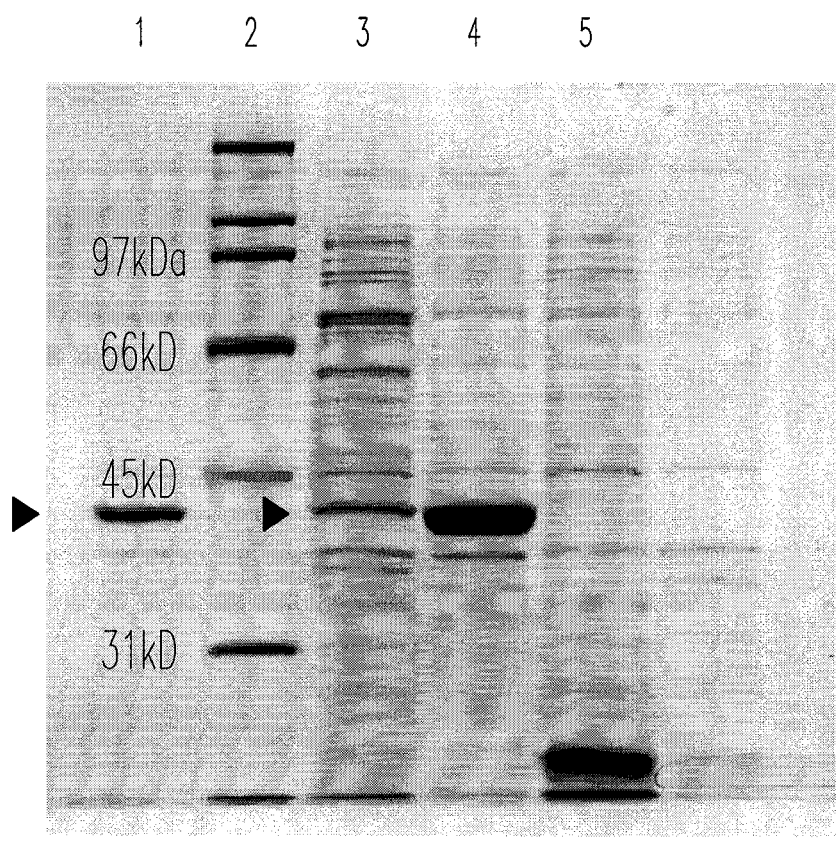
FIG. 24. Analysis of *E. coli* lysates. Lane 1) 0.5 µL insoluble fraction* of Rosetta gami B(DE3)/pET-GO#11; lane 2) MW marker; lane 3) 2.0 µL cell extract of Rosetta gami B(DE3)/pET-GO#11 (7.4 µg of protein); lane 4) 2.0 µL insoluble fraction of Rosetta gami B(DE3)/pET-GO#11; lane 5) 5.3 µL cell extract of Rosetta gami B(DE3)/pET-32a, a control strain (7.4 µg of protein); and lane 6) 5.3 µL insoluble fraction of Rosetta gami B(DE3)/pET-32a. * After lysing the cells by French Press, the lysate was centrifuged at 25,800×g for 10 minutes, and the resulting supernatant (about 10 mL) was saved as the cell extract. The pellet was suspended in 10 mL PBS and considered to be the insoluble fraction.
Figure 25A:
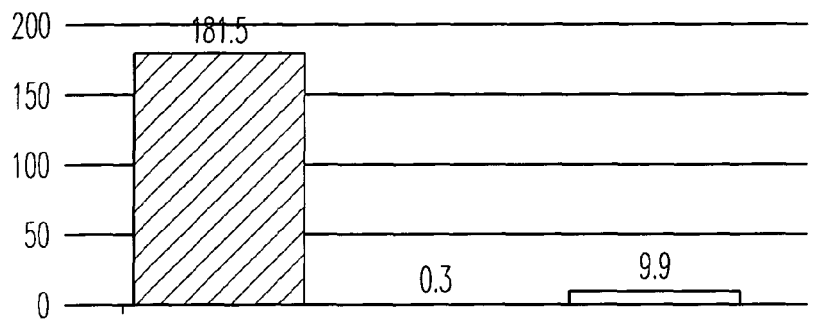
FIGS. 25A-B. A) Glycolate oxidase activity in Rosetta gami B(DE3)/pET-GO#11 cell extract. B) Glycolate oxidase activity in Rosetta gami B(DE3) cell extract.
Figure 25B:
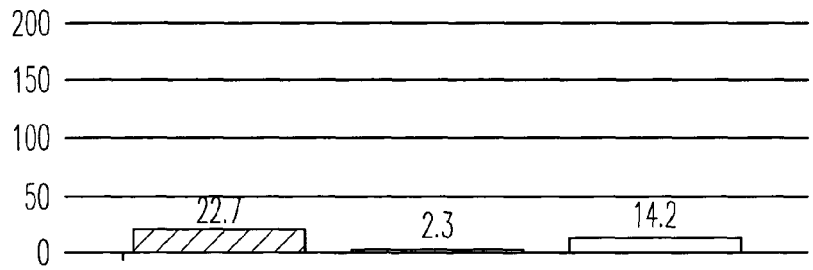
Figure 26:
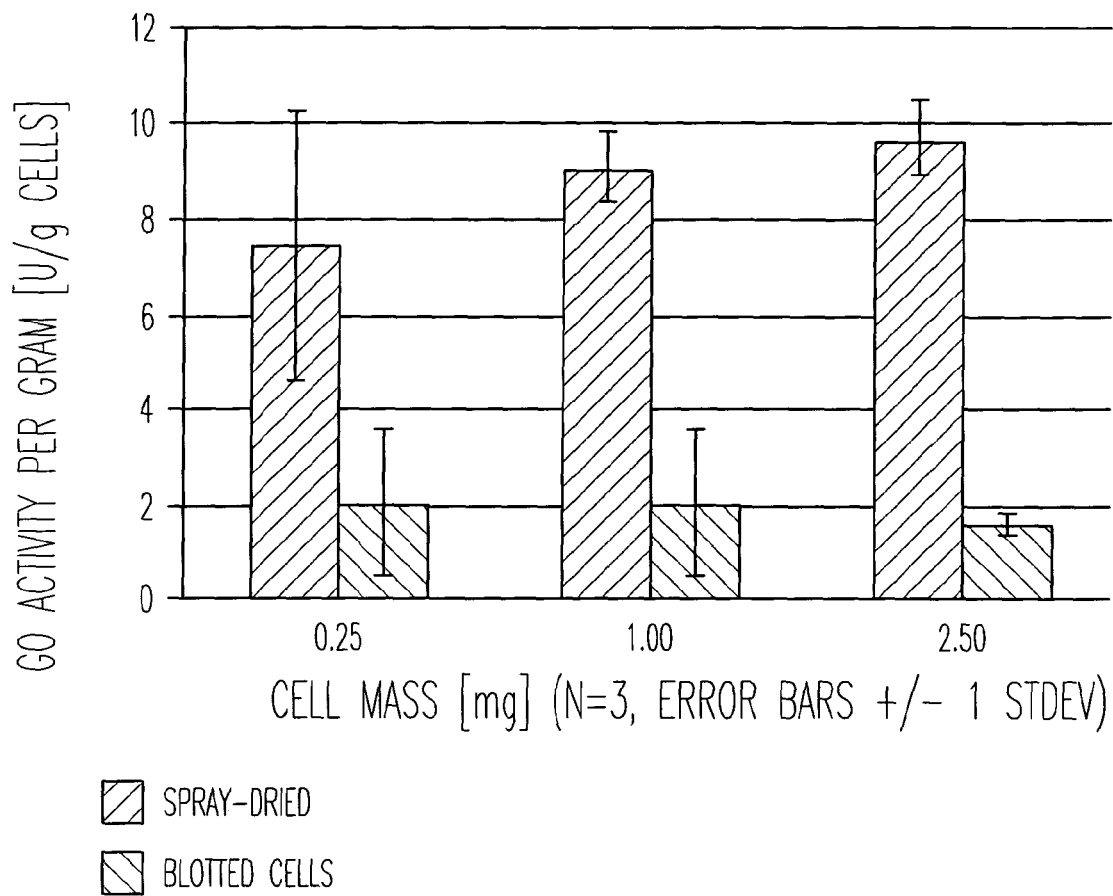
FIG. 26. Glycolate oxidase activity in spray-dried or blotted Rosetta gami B(DE3)/pET-GO#11 cells.
Figure 27:
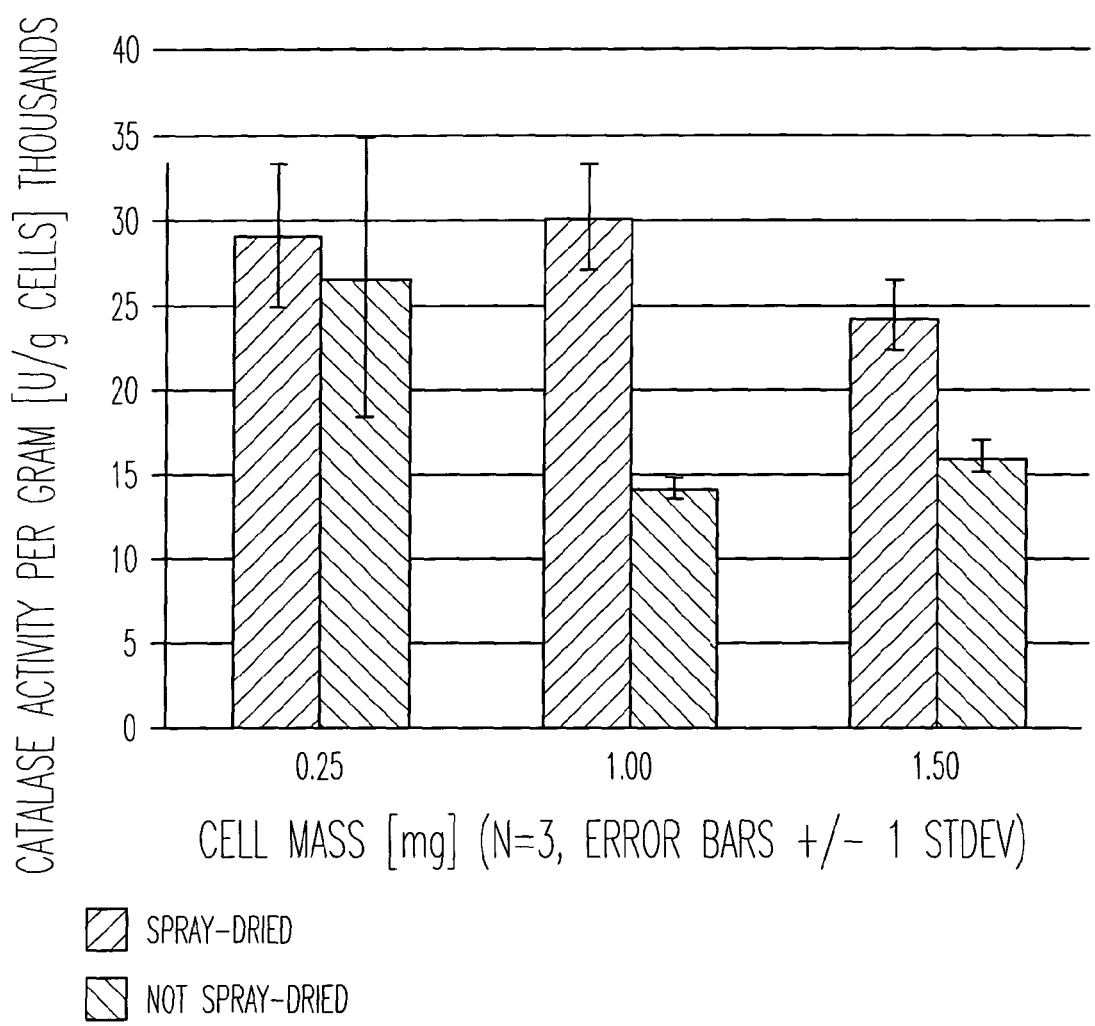
FIG. 27. Catalase activity in spray-dried or control *S. cerevisiae* cells.

A 5 mL seed culture of Rosetta-gami B(DE3)/pET-GO#11 cells was grown in LB medium supplemented with ampicillin (100 μg/mL) and chloramphenicol (34 μg/mL) at 37° C. for 16 hours. The seed culture was used to inoculate 250 mL LB-ampicillin-chloramphenicol medium to an initial cell density of 0.01 $OD_{600}$ (optical density at 600 nm) units. The culture was incubated at 30° C. with shaking at 230 rpm, until the $OD_{600}$ value reached 0.3. Incubation was continued at 24° C. with shaking at 230 rpm until the $OD_{600}$ value reached 0.5 to 0.6. Isopropyl-β-D-thiogalactopyranoside (IPTG) was then added to the culture (final concentration of 0.2 mM) to induce GO protein production. The induced culture was incubated at 24° C. with shaking at 230 rpm for 16 hours. The cells were harvested by centrifugation at 10,000×g, 4° C. for 10 minutes. The cell pellet was then suspended in 10 mL phosphate buffered saline (PBS) plus 1 mM dithiothreitol and 1 mM phenylmethylsulfonyl fluoride. The cells were disrupted by passing through a chilled French pressure cell two times at 260 MPa. The lysate was centrifuged at 25,800×g 4° C. for 10 minutes, and supernatant that contained 3.7 mg of protein/mL (determined by Bradford assay with BSA as standard) was saved as a cell extract for a GO activity assay (FIG. 25) and SDS-PAGE analysis (FIG. 24).

GO activity of a Rosetta-gami B(DE3)/pET-GO#11 cell extract was measured as described above. GO activity of a Rosetta-gami B(DE3)/pET-GO#11 cell extract was tested (a) with substrate (lactate), (b) without substrate, and (c) with substrate and a thermally denatured extract (by boiling extract at 110° C. for 10 minutes). These results were compared to a control extract from Rosetta-gami B(DE3) cells without the pET-GO#11 plasmid under the same assay conditions. Results were plotted in enzyme activity units (U)/mg protein.

The Rosetta-gami B(DE3)/pET-GO#11 soluble fraction had sufficient GO activity to generate more cell mass for spray-drying. A 100 mL seed culture of Rosetta-gami B(DE3)/pET-GO#11 cells were grown in LB medium supplemented with ampicillin (100 μg/mL) and chloramphenicol (34 μg/mL) at 37° C. for 16 hours. The seed culture was used to inoculate 500 mL LB-ampicillin-chloramphenicol medium to an initial cell density of 0.1 $OD_{600}$ (optical density at 600 nm) units. The culture was incubated at 29° C. with shaking at 180 rpm, until the $OD_{600}$ value reached 0.3. Incubation was continued at 25° C. with shaking at 230 rpm until the $OD_{600}$ value reached 0.5 to 0.6. Isopropyl-β-D-thiogalactopyranoside (IPTG) was then added to the culture (final concentration of 0.2 mM) to induce GO protein production. The induced culture was incubated at 25° C. with shaking at 230 rpm for 16 hours. The cells were harvested by centrifugation at 10,000×g, 4° C. for 10 minutes. The cell pellet was stored at −80° C. while the above growth procedure was repeated to generate a total of 11 g wet cell weight for spray-drying studies.

The Rosetta-gami B(DE3)/pET-GO#11 cells were thawed at 4° C. The 11 g cell pellet was divided into two parts: 10 g were spray-dried, and the remaining 1 g was kept as a control. The 10 g of cells were diluted with deionized water to a total volume of 40 mL. This yielded a cell concentration of 250 mg/mL for the spray-dryer feed. Spray-dryer operating conditions were 15 mL/minute feed rate, 600 L/hour air flow rate, and 150° C. inlet air temperature. The resulting biocatalyst powder was collected for GO activity analysis. The remaining 1 g Rosetta-gami B(DE3)/pET-GO#11 cells (not spray-dried) were blotted on Whatman #2 filter paper to remove excess moisture. The spray-dried cells and blotted (control) cells were assayed for GO activity as described hereinabove. Results for spray-dried cells and blotted cells are shown in U/mg dry cell weight and U/mg blotted cell weight, respectively. Three cell masses were tested for each cell preparation method and GO activity was calculated on a per gram basis. The lowest cell mass (0.25 mg) was near the sensitivity limits of the spectrophotometer, resulting in higher error for the initial data point. The spray-dried Rosetta-gami B(DE3)/pET-GO#11 cells retained nearly 10 activity units per gram dry cells (FIG. 26). With additional optimization of spray-drying parameters, i.e., operating temperature, feed rate, and feed cell concentration, further GO activity could be achieved in spray-dried Rosetta-gami B(DE3)/pET-GO#11 cells.

Another organism, *Saccharomyces cerevisiae*, containing native catalase enzyme, was spray-dried and tested for catalase activity. *S. cerevisiae* was obtained from SAF-Instant Company as a granular free-flowing yeast for use in baking doughs with short fermentation processes. 10 g of granular *S. cerevisiae* cells were diluted with deionized water to a total volume of 100 mL. This yielded a cell concentration of 100 mg/mL for the spray-dryer feed. Spray-dryer operating conditions were 15 mL/minute feed rate, 600 L/hour air flow rate, and 150° C. inlet air temperature. The resulting biocatalyst powder was collected for catalase activity analysis. Another 40 mg of granular *S. cerevisiae* (not spray-dried) was used as a control. The spray-dried cells and control cells were assayed for catalase activity as described hereinabove; Results for spray-dried cells and control cells were plotted as U/mg dry weight. Three cell masses were tested for each cell preparation method and catalase activity was calculated on a per gram basis. The lowest cell mass (0.25 mg) was near the sensitivity limits of the spectrophotometer, resulting in higher error for the initial data point. The spray-dried SAF-Instant granular *S. cerevisiae* cells retained 25 to 30 thousand activity units per gram dry cells. The *S. cerevisiae* that was not spray-dried may have been subjected to processing conditions by the manufacturer to create the granular yeast, and those conditions could have partially permeabilized the cell membranes and increased catalase activity in the non spray-dried samples.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to prepare a whole recombinant yeast cell biocatalyst preparation, comprising:

a) providing a whole recombinant yeast cell suspension which is up to 400 mg/mL; and b) spray drying the recombinant yeast cell suspension in the absence of a permeabilization agent at a temperature up to 150° C. effective to yield a spray-dried recombinant yeast cell preparation suitable for biocatalysis, wherein the spray-dried cells are porous but retain an enzyme active in the biocatalysis.

2. The method of claim 1 wherein the spray drying includes heating an amount of the cell suspension flowing through an aperature.

3. The method of claim 1 wherein the yeast cell suspension is a *Pichia, Hansenula* or *Saccharomyces* cell suspension.

4. The method of claim 1 wherein the recombinant yeast cell comprises an expression cassette encoding a heterologous glycolate oxidase.

5. The method of claim 4 wherein the recombinant yeast cell comprises an expression cassette encoding a heterologous catalase.

6. The method of claim 1 further comprising separating the suspension into a liquid fraction and a solid fraction which contains the cells prior to spray drying.

7. The method of claim 6 further comprising spray drying the separated cells.

8. The method of claim 6 wherein the suspension is separated by centrifugation.

9. The method of claim 6 wherein the suspension is separated using a membrane.

10. A spray-dried recombinant yeast cell preparation prepared by the method of claim 1.

11. The preparation of claim 10 wherein the yeast is *Pichia*.

12. The preparation of claim 10 wherein the recombinant yeast comprises at least one recombinant enzyme.

13. The preparation of claim 12 wherein the recombinant enzyme is a heterologous glycolate oxidase.

14. The preparation of claim 12 wherein the recombinant enzyme is a heterologous catalase.

15. The preparation of claim 10 wherein the recombinant yeast has a genome that is augmented or a portion of the genome that is replaced with an expression cassette.

16. A method to prepare products of an enzymatic reaction, comprising:
   a) providing the spray-dried preparation of claim 10; and
   b) combining the preparation and an aqueous solution comprising a substrate for an enzyme in the preparation under conditions that yield a product of the enzyme catalyzed reaction.

17. The method of claim 16 wherein the enzyme is glycolate oxidase.

18. The method of claim 17 wherein the product is pyruvate or glyoxylate.

19. The method of claim 16 wherein the products are keto acids or chiral hydroxyl acids.

20. The method of claim 16 further comprising isolating the product.

* * * * *